US009738617B2

United States Patent
(12) United States Patent
Sacia et al.

(10) Patent No.: US 9,738,617 B2
(45) Date of Patent: Aug. 22, 2017

(54) METHODS FOR PRODUCING FUELS, GASOLINE ADDITIVES, AND LUBRICANTS

(71) Applicants: The Regents of the University of California, Oakland, CA (US); BP Corporation North America Inc., Houston, TX (US)

(72) Inventors: Eric Sacia, Wilmington, DE (US); Anbarasan Pazhamalai, Cuddalore (IN); Balakrishnan Madhesan, Fremont, CA (US); Sanil Sreekumar, Midland, MI (US); F. Dean Toste, Piedmont, CA (US); Amit A. Gokhale, El Cerrito, CA (US); Martin E. Carrera, San Diego, CA (US); Alexis T. Bell, Oakland, CA (US); Gorkem Gunbas, Ankara (TR)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 0 days.

(21) Appl. No.: 14/895,851

(22) PCT Filed: Jun. 3, 2014

(86) PCT No.: PCT/US2014/040760

§ 371 (c)(1),
(2) Date: Dec. 3, 2015

(87) PCT Pub. No.: WO2014/197514

PCT Pub. Date: Dec. 11, 2014

(65) Prior Publication Data

US 2016/0115143 A1 Apr. 28, 2016

Related U.S. Application Data

(60) Provisional application No. 61/830,586, filed on Jun. 3, 2013.

(51) Int. Cl.
*C07D 307/02* (2006.01)
*C07C 1/20* (2006.01)
(Continued)

(52) U.S. Cl.
CPC .......... *C07D 307/46* (2013.01); *C07C 1/2076* (2013.01); *C07C 1/22* (2013.01);
(Continued)

(58) Field of Classification Search
CPC ..... C07D 307/46; C10L 1/182; C10L 1/1608; C10L 1/06; C10L 1/08; C10L 2200/0423;
(Continued)

(56) References Cited

FOREIGN PATENT DOCUMENTS

| | | | |
|---|---|---|---|
| CN | 102019177 | A | 4/2011 |
| CN | 102188967 | A | 9/2011 |

(Continued)

OTHER PUBLICATIONS

International Search Report and Written Opinion Received for PCT Patent Application No. PCT/US2014/040760 mailed on Nov. 25, 2014, 19 pages.

(Continued)

*Primary Examiner* — T. Victor Oh
(74) *Attorney, Agent, or Firm* — Morrison & Foerster LLP

(57) ABSTRACT

The present disclosure generally relates to the production of fuels, gasoline additives, and/or lubricants, and precursors thereof. The compounds used to produce the fuels, gasoline additives, and/or lubricants, and precursors thereof may be derived from biomass. The fuels, gasoline additives, and/or lubricants, and precursors thereof may be produced by a combination of intermolecular and/or intramolecular aldol condensation reactions, Guerbet reactions, hydrogenation reactions, and/or oligomerization reactions.

14 Claims, 4 Drawing Sheets

(51) Int. Cl.

| | |
|---|---|
| ***C07C 1/00*** | (2006.01) |
| ***C07C 2/00*** | (2006.01) |
| ***C07C 45/00*** | (2006.01) |
| ***C07C 4/00*** | (2006.01) |
| ***C07D 307/46*** | (2006.01) |
| ***C07C 29/17*** | (2006.01) |
| ***C07C 1/22*** | (2006.01) |
| ***C07C 45/66*** | (2006.01) |
| ***C07C 45/71*** | (2006.01) |
| ***C07C 45/74*** | (2006.01) |
| ***C10G 3/00*** | (2006.01) |
| ***C07C 1/207*** | (2006.01) |
| ***C07C 45/68*** | (2006.01) |
| ***C07C 45/72*** | (2006.01) |
| ***C10L 1/06*** | (2006.01) |
| ***C10L 1/08*** | (2006.01) |
| ***C10L 1/16*** | (2006.01) |
| ***C10L 1/182*** | (2006.01) |
| ***C10M 127/02*** | (2006.01) |
| ***C10M 129/06*** | (2006.01) |

(52) U.S. Cl.

CPC ............ *C07C 29/175* (2013.01); *C07C 45/66* (2013.01); *C07C 45/68* (2013.01); *C07C 45/71* (2013.01); *C07C 45/72* (2013.01); *C07C 45/74* (2013.01); *C10G 3/50* (2013.01); *C10L 1/06* (2013.01); *C10L 1/08* (2013.01); *C10L 1/1608* (2013.01); *C10L 1/182* (2013.01); *C10M 127/02* (2013.01); *C10M 129/06* (2013.01); *C07C 2101/08* (2013.01); *C07C 2101/10* (2013.01); *C07C 2523/42* (2013.01); *C07C 2523/44* (2013.01); *C07C 2523/46* (2013.01); *C10L 2200/0423* (2013.01); *C10L 2200/0446* (2013.01); *C10L 2270/023* (2013.01); *C10L 2270/026* (2013.01); *C10M 2203/022* (2013.01); *C10M 2203/04* (2013.01); *C10M 2207/021* (2013.01); *C10N 2270/00* (2013.01); *Y02P 30/20* (2015.11)

(58) Field of Classification Search

CPC ....... C10L 2200/0446; C10L 2270/023; C10L 2270/026; C10M 127/02; C10M 129/06; C10M 2203/04; C10M 2203/022; C10M 2207/021; C07C 1/2076; C07C 1/22; C07C 29/175; C07C 45/68; C07C 45/66; C07C 45/72; C07C 45/71; C07C 45/74; C07C 2101/08; C07C 2101/10; C07C 2523/42; C07C 2523/44; C07C 2523/46; C10G 3/50; C10N 2270/00; Y02P 30/20

USPC ........ 549/472; 568/379, 390, 391, 465, 485; 585/310, 317, 357, 733

See application file for complete search history.

(56) References Cited

FOREIGN PATENT DOCUMENTS

| | | | |
|---|---|---|---|
| CN | 102389829 | A | 3/2012 |
| CN | 102600827 | A | 7/2012 |
| EP | 0444460 | A2 | 9/1991 |
| WO | 9719905 | A1 | 6/1997 |
| WO | 2012166267 | A2 | 12/2012 |

OTHER PUBLICATIONS

Ayame et al., "Alumina Solid Lewis Superacid: Activated Benzene and Isomerization of Alkanes on Aluminas Chlorinated at High Temperature", Journal of the Chemical Society, Chemical Communications,1989, pp. 645-646.

Schlenk, "Beitrag Zur Kenntnis Der Polyen-Diketone", Jahrg, vol. 81, 1948, pp. 175-178.

Stetter et al., "Addition Von Aldehyden an Aktivierte Doppelbindungen, XIX. Darstellung Von Ungesattigten", Chemische Berichte, vol. 112, 1979, pp. 84-94.

Iuchi et al., "Synthesis of [omega]-Hydroxy Carboxylic Acids and [alpha],[omega]-Dimethyl Ketones using [alpha],[omega]-Diols as Alkylating Agents", The Journal of Organic Chemistry, vol. 75, No. 5, 2010, pp. 1803-1806.

Kretchmer et al., "A New Furan Synthesis", The Journal of Organic Chemistry, vol. 43, No. 24, 1978, pp. 4596-4598.

Nakatsu et al., "A Convenient Synthesis of Olefins Via Deacylation Reaction", Tetrahedron, vol. 60, 2004, pp. 2337-2349.

Qiu et al., "Synthesis and Evaluation of Curcumin Analogues as Potential Thioredoxin Reductase Inhibitors", Bioorganic & Medicinal Chemistry, vol. 16, 2008, pp. 8035-8041.

Tan et al., "Advances in Catalyst of Aidol Condensation", Chemical Industry and Engineering, vol. 23, No. 1, Jan. 2006, pp. 70-74 (English Abstract Submitted).

METHODS FOR PRODUCING FUELS, GASOLINE ADDITIVES, AND LUBRICANTS

CROSS-REFERENCE TO RELATED APPLICATIONS

This application is a U.S. national stage application of PCT/US2014/040760, filed internationally on Jun. 3, 2014, which claims priority to U.S. Provisional Patent Application No. 61/830,586, filed Jun. 3, 2013, which are incorporated herein by reference in their entireties.

FIELD

The present disclosure generally relates to the production of fuels, gasoline additives, and/or lubricants, and precursors thereof.

BACKGROUND

Producing fuels and other value added chemicals such as gasoline additives and lubricants from renewable sources has become increasingly important as a means of reducing the production of greenhouse gases and of reducing the imports of petroleum. See L. D. Gomez, C. G. Steele-King, S. J. McQueen-Mason, *New Phytologist,* 2008, 178, 473-485. Lignocellulosic biomass is typically made up of cellulose, hemicellulose, and lignin. These biomass components are non-edible, carbohydrate-rich polymers that may serve as a renewable source of energy. They typically make up to at least 70% of the dry weight of biomass. As such, conversion of these non-edible biomass components into biofuels and other value added chemicals from renewable sources is of ongoing interest that can benefit the environment and reduce petroleum imports. See A. Demirbas, *Energy Sources, Part B: Economics, Planning and Policy,* 2008, 3, 177-185. Biomass may first be converted to intermediate compounds such as sugars, which may then be converted into other precursor molecules that may be converted to fuels (e.g., gasoline or diesel), gasoline additives, and/or lubricants.

BRIEF SUMMARY

In one aspect, provided is a method of producing one or more ketones by contacting a compound of formula (I) with basic catalyst and one or more alcohols or aldehydes of formula (II) to produce the one or more ketones, wherein the compound of formula (I) and the compound of formula (II) have the following structures:

(I) + (II);

wherein:

each $R_1$, $R_2$, $R_3$, $R_4$, $R_5$, and $R_6$ is independently selected from hydrogen, alkyl, aryl, alkenyl, and alkynyl; provided that one or both of (i) and (ii) occurs: (i) at least two of $R_1$, $R_2$, and $R_3$ are hydrogen; and (ii) at least two of $R_4$, $R_5$, and $R_6$ are hydrogen;

n is an integer greater than or equal to 0;

$R_7$ is selected from alkyl, aryl, alkenyl, alkynyl, and heteroaryl;

X is OH or O; and the dashed line represents an optional double bond that is present when X is O.

In another aspect, provided is a method of producing one or more $C_{24}$-$C_{36}$ alkanes, by: (a) contacting an aldehyde and one or more alcohols with metal catalyst and optionally base to produce one or more higher aldehydes; (b) hydrogenating the one or more higher aldehydes to one or more higher alcohols; and (c) converting the one or more higher alcohols to the one or more $C_{24}$-$C_{36}$ alkanes. In some embodiments, the higher aldehydes have a greater number of carbon atoms than the number of carbon atoms in the ketone used in step (a) as a starting material.

In yet another aspect, provided is a method of producing one or more compounds of formula (IX), by contacting a ketone of formula (VII) with a diol of formula (VIII) to produce the one or more compounds of formula (IX), wherein:

the ketone of formula (VII) has the following structure:

(VII)

wherein:

$R_{14}$ is H or alkyl; and $R_{15}$ is methyl;

the diol of formula (VIII) has the following structure:

(VIII)

wherein t is an integer greater than or equal to 4; and the one or more compounds of formula (IX) have the following structure:

(IX)

wherein:

$R_{14}$ is as described above for formula (VII)

$R_{16}$ is —$CH_2$—; and t is as described above for formula (VIII).

In yet another aspect, provided is a method of producing a cyclic alkane, cyclic alcohol, or mixtures thereof, by: (a) contacting a diketone with basic catalyst to produce a cyclic ketone; and (b) hydrogenating the cyclic ketone to produce the cyclic alkane, cyclic alcohol, or mixtures thereof.

Provided is also a composition that includes: a diesel fuel, a gasoline additive, or a lubricant, or any mixtures thereof; and one or more alkanes, cyclic alkanes, or cyclic alcohols produced according to any of the methods described above.

DESCRIPTION OF THE FIGURES

The present application can be understood by reference to the following description taken in conjunction with the accompanying drawing figures, in which like parts may be referred to by like numerals.

DETAILED DESCRIPTION

Figure 1:
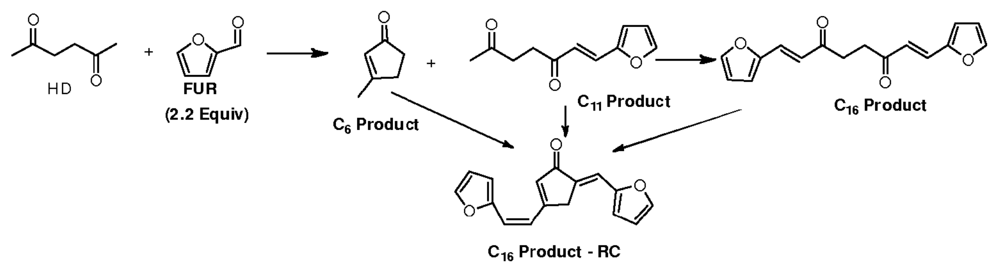
FIG. 1 depicts the data obtained for the cross-aldol condensation of 2,5-hexanedione and furfural at 25° C., 50° C., and 80° C.
Figure 1:
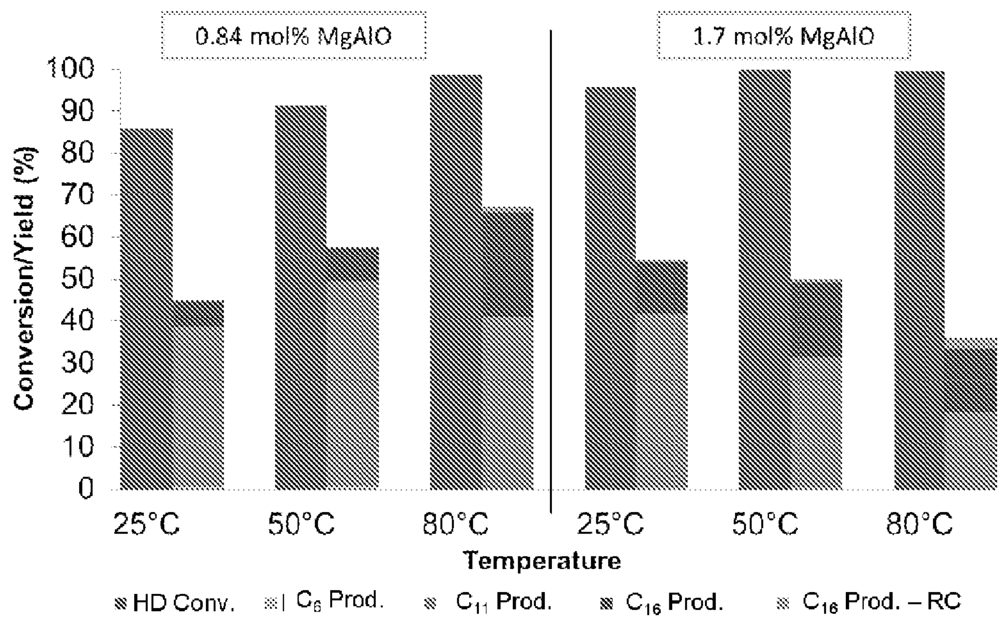

The following description sets forth numerous exemplary configurations, processes, parameters, and the like. It should be recognized, however, that such description is not intended as a limitation on the scope of the present disclosure, but is instead provided as a description of exemplary embodiments.

Definitions

"Alkyl" refers to a monoradical unbranched or branched saturated hydrocarbon chain. In some embodiments of the compounds disclosed herein, the alkyl has 1 to 20 carbon atoms (i.e., $C_1$-$C_{20}$ alkyl), 1 to 10 carbon atoms (i.e., $C_1$-$C_{10}$ alkyl), 1 to 8 carbon atoms (i.e., $C_1$-$C_8$ alkyl), 1 to 6 carbon atoms (i.e., $C_1$-$C_6$ alkyl), or 1 to 4 carbon atoms (i.e., $C_1$-$C_4$ alkyl). Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, isobutyl and t-butyl; "propyl" can include n-propyl and isopropyl. The term "alkyl" also includes "cycloalkyl" compounds. "Cycloalkyl" refers to a cyclic alkyl group. In some embodiments of the compounds of formula (I), cycloalkyl has from 3 to 20 ring carbon atoms (i.e., $C_3$-$C_{20}$ cycloalkyl), or 3 to 12 ring carbon atoms (i.e., $C_3$-$C_{12}$ cycloalkyl), or 3 to 8 ring carbon atoms (i.e., $C_3$-$C_8$ cycloalkyl). Examples of cycloalkyl groups include cyclopropyl, cyclobutyl, cyclopentyl, and cyclohexyl.

"Alkenyl" refers to an unsaturated hydrocarbon group having at least one site of olefinic unsaturation (i.e., having at least one moiety of the formula C═C).

"Alkynyl" refers to an unsaturated hydrocarbon group having at least one site of acetylenic unsaturation (i.e., having at least one moiety of the formula C≡C).

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments of the compounds disclosed herein, aryl has 6 to 20 ring carbon atoms (i.e., $C_6$-$C_{20}$ aryl), or 6 to 12 carbon ring atoms (i.e., $C_6$-$C_{12}$ aryl).

"Heteroaryl" refers to an aryl group, wherein at least one carbon atom of the designated carbocyclic group has been replaced by a heteroatom selected from N, O and S. The term also includes five-membered heteroaromatic rings such as, for example, furans and imidazoles.

Provided herein are methods of producing gasoline additives, diesel, and/or lubricants, and precursors thereof. In some embodiments, a diketone can undergo cross-aldol condensation with an aldehyde or alcohol to yield diesel precursors, which could be hydrogenated to form high value diesel. The products of the cross-aldol condensation could also undergo other types of chemistry, such as Guerbet chemistry, to yield lubricants. In other embodiments, a diketone can undergo intramolecular cyclization to form a gasoline precursor, which could be hydrogenated to form gasoline additives.

The reactions to produce gasoline additives, diesel, and/or lubricants, and precursors thereof, are each described in more detail below.

Cross-Aldol Condensation of Compounds of Formula (I) and Compounds of Formula (II)

In one aspect, provided is a method of producing one or more ketones by contacting a compound of formula (I) with basic catalyst and one or more alcohols or aldehydes of formula (II) to produce the one or more ketones:

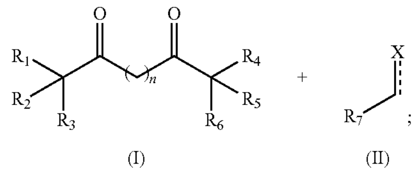

wherein:

each $R_1$, $R_2$, $R_3$, $R_4$, $R_5$, and $R_6$ is independently selected from hydrogen, alkyl, aryl, alkenyl, and alkynyl; provided that one or both of (i) and (ii) occurs: (i) at least two of $R_1$, $R_2$, and $R_3$ are hydrogen; and (ii) at least two of $R_4$, $R_5$, and $R_6$ are hydrogen;

$R_7$ is selected from alkyl, aryl, alkenyl, alkynyl, and heteroaryl;

X is OH or O; and n is an integer greater than or equal to 0.

It should be understood that, with respect to the alcohols or aldehydes of formula (II), the dashed line represents an optional double bond that is present when X is O, or an optional double bond that is not present when X is OH.

a) Compounds of Formula (I)

Compounds of formula (I) have the structure:

(I)

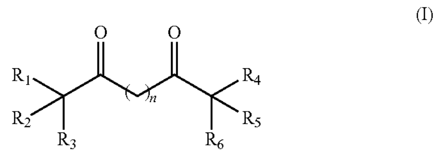

wherein:

each $R_1$, $R_2$, $R_3$, $R_4$, $R_5$, and $R_6$ is independently hydrogen, alkyl, aryl, alkenyl, or alkynyl; provided that (i) at least two of $R_1$, $R_2$, and $R_3$ is hydrogen, (ii) at least two of $R_4$, $R_5$, and $R_6$ is hydrogen, or a combination thereof; and n is an integer greater than or equal to 0.

In some embodiments, each $R_1$, $R_2$, $R_3$, $R_4$, $R_5$, and $R_6$ is independently hydrogen, $C_1$-$C_{20}$ aryl, $C_6$-$C_{22}$ aryl, $C_2$-$C_{20}$ alkenyl, or $C_2$-$C_{20}$ alkynyl. In certain embodiments, each $R_1$, $R_2$, $R_3$, $R_4$, $R_5$, and $R_6$ is independently hydrogen, $C_1$-$C_{10}$ alkyl, $C_6$-$C_{22}$ aryl, $C_2$-$C_{10}$ alkenyl, or $C_2$-$C_{10}$ alkynyl. In certain embodiments, each of $R_1$, $R_2$, $R_3$, $R_4$, $R_5$, and $R_6$ is hydrogen, such that the compound of formula (I) has the structure:

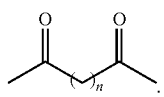

In some embodiments, n is an integer greater than or equal to 1. In certain embodiments, n is 1-20, 1-15, 1-10, or 2-5.

In one embodiment, the compound of formula (I) is 2,5-hexanedione, having the structure:

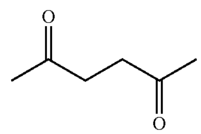

The compounds of formula (I) can be obtained from any commercially available source, or according to any methods known to one of skill in the art. The compounds of formula (I) can be obtained from biomass. For example, cellulose or hemicellulose may first be converted to glucose or xylose, which then may be converted to 5-hydroxymethylfufural or furfural. The 5-hydroxymethylfurfural can be converted to 2,5-dimethylfuran, which can be hydrolyzed under acidic conditions to yield 2,5-hexanedione. See e.g., Thananatthanachon and Rauchfuss, *Angewandte Chemie International Edition* 2010, 49 (37), 6616-6618; Kuhlmann, et al., *The Journal of Organic Chemistry* 1994, 59 (11), 3098-3101.

b) Compounds of Formula (II)

Compounds of formula (II) have the structure:

(II)

X;

$R_7$ wherein:

$R_7$ is $C_1$-$C_{20}$ alkyl, $C_6$-$C_{20}$ aryl, $C_2$-$C_{20}$ alkenyl, $C_2$-$C_{20}$ alkynyl, or $C_4$-$C_{21}$ heteroaryl;

X is OH or O; and the dashed line represents an optional double bond that is not present when X is OH.

In some embodiments, X is OH and the compound of formula (II) is a compound of formula (II-A):

(II-A)

OH.

$R_7$

In other embodiments, X is O and the compound of formula (II) is a compound of formula (II-B):

(II-B)

O.

$R_7$

In some embodiments, $R_7$ is $C_1$-$C_{20}$ alkyl, $C_6$-$C_{22}$ aryl, $C_2$-$C_{20}$ alkenyl, $C_2$-$C_{20}$ alkynyl, and $C_4$-$C_{21}$ heteroaryl. In certain embodiments, $R_7$ is $C_1$-$C_{10}$ alkyl, $C_6$-$C_{22}$ aryl, $C_2$-$C_{10}$ alkenyl, $C_2$-$C_{10}$ alkynyl, and $C_4$-$C_{21}$ heteroaryl. In certain embodiments, $R_7$ is $C_1$-$C_{10}$ alkyl. In one embodiment, $R_7$ is $C_4$ alkyl. In other embodiments, $R_7$ is heteroaryl. In one embodiment, $R_7$ is furanyl. In other embodiments, $R_7$ is furfural, 5-methylfurfural, or 5-hydroxymethylfurfural.

In one embodiment, the compound of formula (II) is:

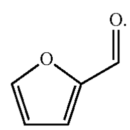

The compounds of formula (II) can be obtained from any commercially available source, or according to any methods known to one of skill in the art. For example, furfural can be obtained from any biomass source. See e.g., Huber, et al., *Chem. Rev.* 2006, 106 (9), 4044-4098.

c) Cross-Aldol Condensation Products

One or more ketones are produced when a compound of formula (I) is contacted with one or more alcohols or aldehydes of formula (II) and a basic catalyst. Depending on various factors, the ketones produced can be the result of an intermolecular reaction between the compounds of formulae (I) and (II), an intramolecular reaction involving the cyclization of the compound of formula (I), or a combination thereof.

Intermolecular Reaction

When the ketones produced are the result of an intermolecular reaction, such ketones may be suitable for use as diesel precursors, including, for example, $C_{11}$-$C_{16}$ diesel precursors. Such an intermolecular reaction may be depicted as follows:

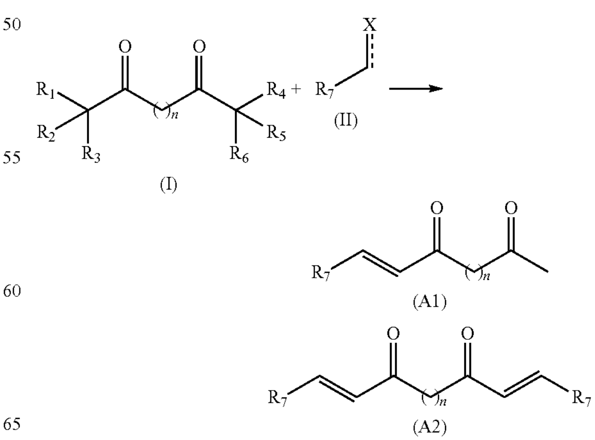

In some embodiments, the intermolecular reaction is:

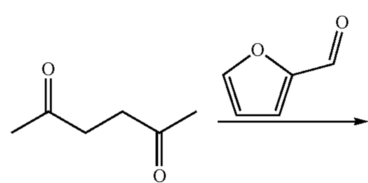

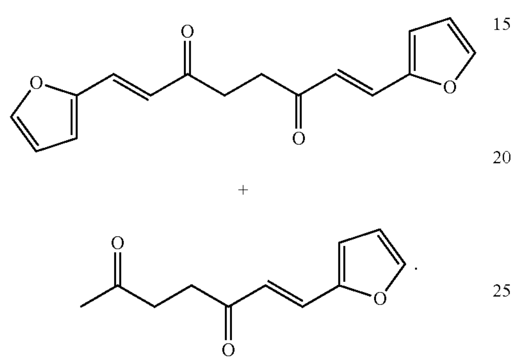

In some embodiments, the ketones produced by the intermolecular reaction are selected from:

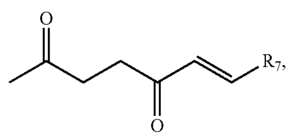

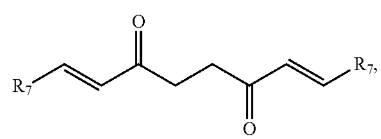

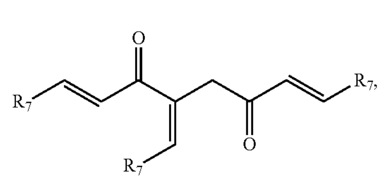

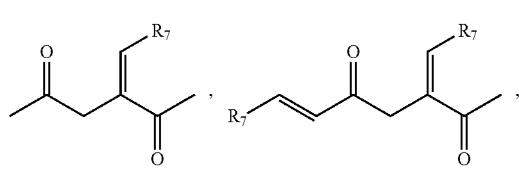

-continued

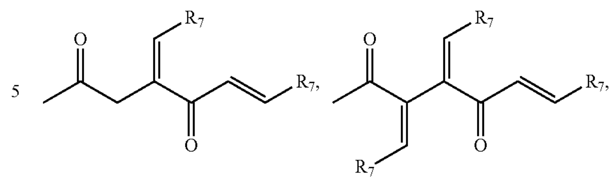

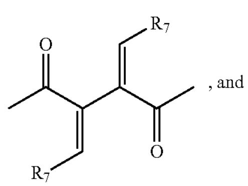

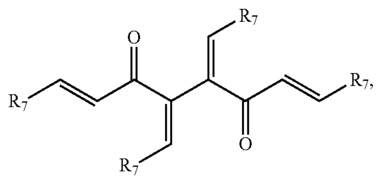

or any mixtures thereof.

In certain embodiments, the intermolecular reaction may yield 1-addition products, including for example:

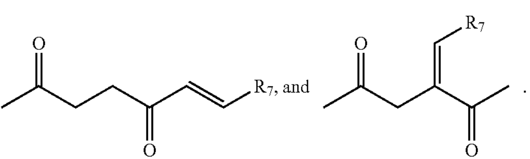

It should be understood, however, that the products may also undergo further aldol condensation to form other oligomers if the product contains enolizable carbons that may continue to react.

For example, the 1-addition products may further react to yield various 2-addition products:

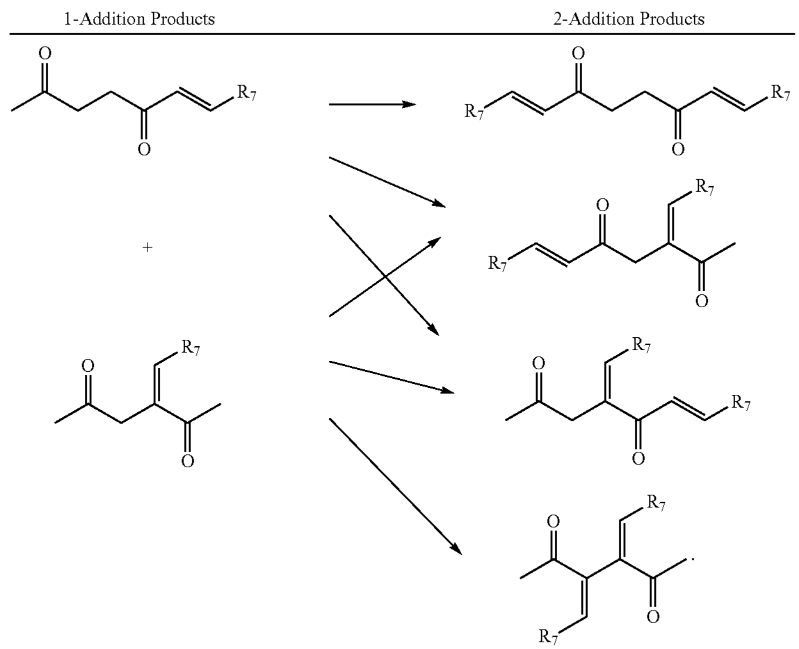
In another example, the 2-addition products may further react to yield various 3-addition products:
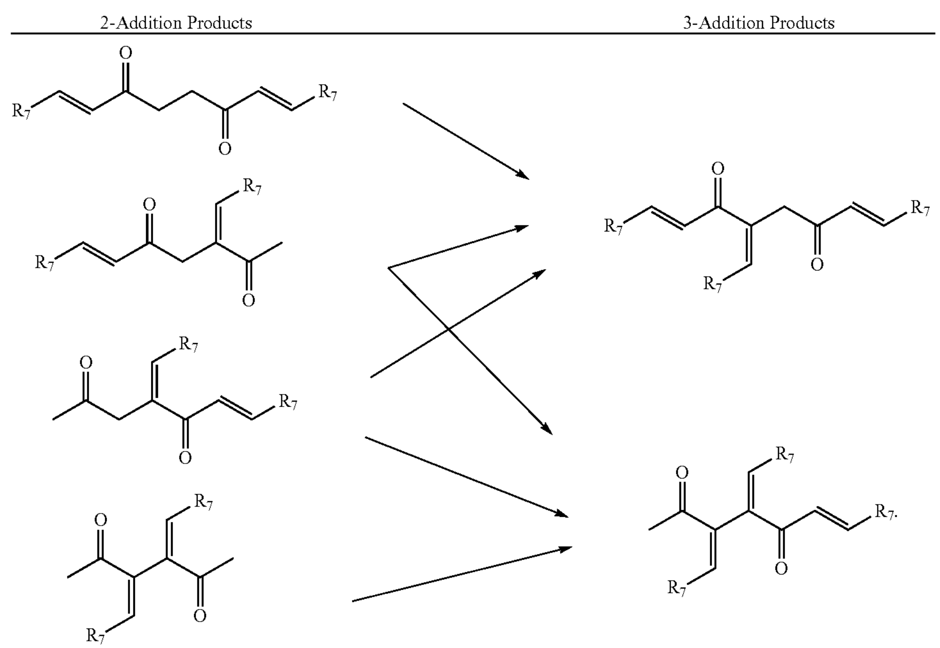
In yet another example, the 3-addition products may further react to yield various 4-addition products:

| 3-Addition Products | 4-Addition Products |
| --- | --- |

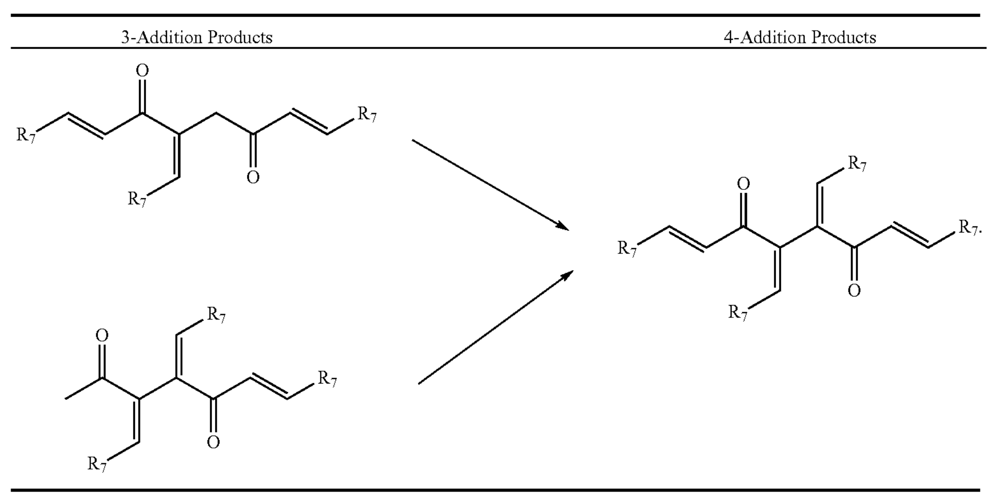

Intramolecular Reaction

When the ketones produced are the result of an intramolecular reaction, such ketones may be suitable for use as gasoline additive precursors, such as compounds of formula (B1), (B2), or a combination thereof:

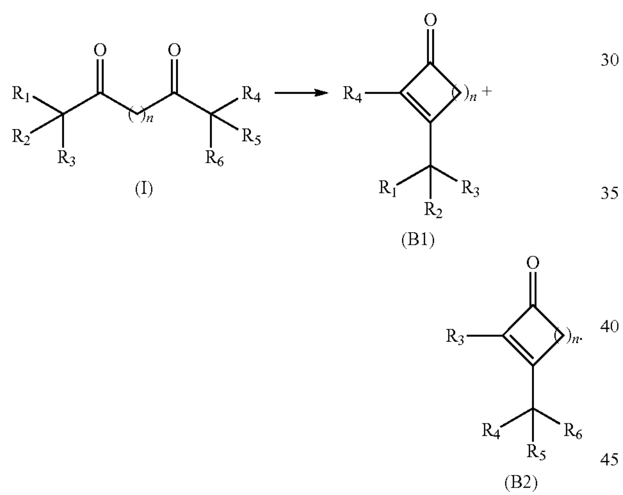

In some embodiments, the intramolecular reaction is:

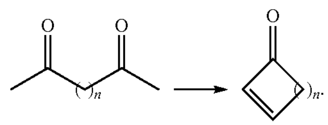

In one embodiment, the intramolecular reaction is:

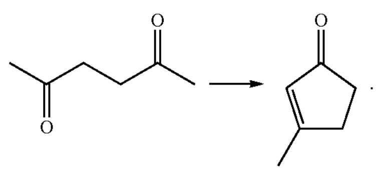

In some embodiments, where the gasoline additives are the desired products, the compound of formula (I) will be converted to compounds of formula B1 and B2 with the basic catalyst in the absence of any compound of formula (II). In some embodiments in reactions with compounds of formula (I) and formula (II), the ketones produced by intramolecular reaction of the compound of formula (I) may react further with a compound of formula (II) to produce compounds of formula (C) that are selected from:

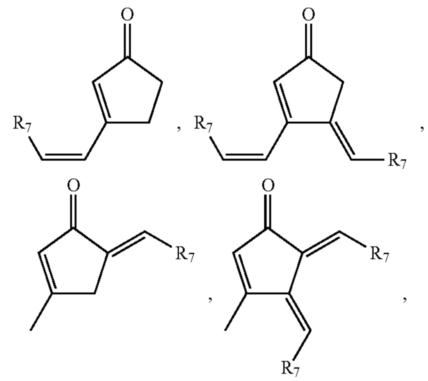

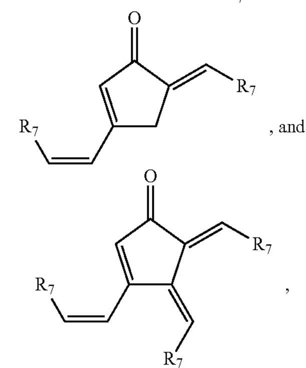

and any mixtures thereof.

It will be understood that the compounds shown above will be formed in an exemplary reaction where the compound of formula (I) is 2,5-hexanedione. The 2,5-hexanedione may undergo intramolecular cyclization followed by condensation with a compound of formula (II). However, any compound of formula (I) may undergo such a cyclization followed by condensation.

It should be understood that that the intermolecular and intramolecular reactions are competing reactions, and product formation can be tuned by controlling one or more factors. Such factors may include, for example, the amount of compound of formula (II) present in the reaction system, type of catalyst, catalyst loading, temperature, and solvent. In some embodiments, branched compounds may be formed in preference to linear compounds. In some embodiments, at least 5%, 10%, 20%, 30%, 40%, 50%, 60%, 70%, 80%, or 90% of the one or more ketones produced by the reaction of the compound of formula (I) and formula (II) are branched ketones. In some embodiments, at least 70% of the one or more ketones produced by the reaction of the compound of formula (I) and formula (II) are branched ketones. In some embodiments, at least 80% of the one or more ketones produced by the reaction of the compound of formula (I) and formula (II) are branched ketones. In some embodiments, at least 90% of the one or more ketones produced by the reaction of the compound of formula (I) and formula (II) are branched ketones.

d) Basic Catalyst

The compounds of formula (I) and one or more alcohols or aldehydes of formula (II) are contacted with basic catalyst to yield one or more ketones, by intermolecular reaction and/or intramolecular reaction.

In some embodiments, the basic catalyst is an inorganic base or an organic base. Examples of inorganic bases may include potassium hydroxide, barium hydroxide, cesium hydroxide, sodium hydroxide, strontium hydroxide, calcium hydroxide, lithium hydroxide, rubidium hydroxide, and magnesium hydroxide. In some embodiments, the base is $K_3PO_4$. Examples of organic bases may include triethylamine, trimethylamine, pyridine, and methyl amine. In some embodiments, the amines may be tethered to a heterogeneous support.

The basic catalyst may be homogenous in the reaction system, or heterogeneous in the reaction system. In one embodiment, the basic catalyst is heterogeneous, allowing for ease of recovery of the catalyst from the reaction system. In some embodiments, the heterogeneous catalyst comprises one or more metals selected from the group consisting of Mg, Al, Zr, Ti, Ce, B, Y, and any mixture thereof. In some embodiments, the heterogeneous catalyst further comprises oxygen. In one embodiment, the heterogeneous catalyst may be derived from a hydrotalcite material. Basicity of hydrotalcites can be tuned by varying the magnesium-aluminum ratio, by rehydrating calcined hydrotalcite, and doping hydrotalcite with Na and K. In some embodiments, hydrotalcites are prepared by co-precipitation of alkaline earth metal salts and/or aluminum nitrates in a solution that includes urea or ammonia and ammonium carbonate or potassium hydroxide and potassium carbonate or sodium hydroxide and sodium carbonate. Typically, the hydrotalcite material is calcined at temperatures of about 400° C. to about 800° C. prior to use in the reactions described herein. After calcination, the hydrotalcite material may be referred to as a mixed metal oxide.

In some embodiments, the basic catalyst is a metal oxide. In some embodiments, the metal oxide comprises a metal selected from the group consisting of Mg, Al, Zr, Ti, Ce, B, and Y. In some embodiments, one or more metal oxide may be combined as used as the basic catalyst. Examples of metal oxides include $ThO_2$, $ZrO_2$, ZnO, $TiO_2$, MgO and any mixture thereof. In some embodiments, the basic catalyst is a mixed metal oxide that contains one or more metals. In some embodiments, the basic catalyst is the mixed metal oxide MgAlO or MgZrO. In some embodiments, the basic catalyst is the mixed metal oxide MgAlO. In some embodiments, the mixed metal oxides comprise at least two metals selected from the group consisting of Mg, Al, Zr, Ti, Ce, B, and Y.

In some embodiments, the catalysts include one or more metals, and a basic support. In certain embodiments, the basic catalyst is KF on alumina.

Basicity of heterogeneous catalysts may be determined by a variety of techniques known in the art. For example, basicity of the heterogeneous catalyst can be measured by $CO_2$ temperature-programmed desorption (TPD). In some embodiments, the $CO_2$ TPD is carried out by adsorbing $CO_2$ to the catalyst at room temperature and heating up to 773 K (or similar assay). In some embodiments, preferred heterogeneous catalysts have base site densities measured by $CO_2$ TPD of at least 50 micromoles/gram of catalyst. In other embodiments, all preferred heterogeneous catalysts of all types have base site densities by $CO_2$ TPD of at least 10 micromoles/gram of catalyst. Basicity of the heterogeneous catalyst may also be measured using zero charge determination (Regalbuto), or using the Hammett indicator method.

In some embodiments, the basic catalysts have a pKa from 10 to 16. In other embodiments, the metal catalysts have a pKa from 11 to 15. In some embodiments, the basic catalyst has a $CO_2$ desorption of at least 200° C. Quantitative determination of the pKa and other methods to characterize the basicity of a catalyst support such as hydrotalcite are known in the art. See, e.g., A. Corma, et al., *J. of Catalysis,* 1992, 134, 58 and D. Debecker, et al., *Chem. Eur. J.,* 2009, 15, 3920.

It should be understood that the metal catalyst can be prepared by any methods known to one of skill in the art. For example, impregnation (e.g., incipient wetness impregnation) is one exemplary technique that can be used. In one example, a support such as hydrotalcite), and metal salt such as palladium chloride or copper acetate) can be combined and a solvent such as water is added. The metal salt and support are allowed to react for a period of time between 1 and 24 hours at a temperature between room temperature and 200° C., or more specifically between 50 and 120° C. The reaction mixture may be stirred under a hydrogen atmosphere. The solid catalyst is then filtered and washed with copious amounts of solvent. The solid may then be dried under vacuum at a temperature between 80 and 150° C. Optionally, other additives may be added to the reaction mixture such as alkali metal salts (e.g., sodium chloride or potassium chloride) or base as described above.

The metal catalyst may also be prepared by impregnation (e.g., incipient wetness impregnation) of metal salts on basic supports, followed by calcination at temperatures higher than 300° C. in air or inert gases and/or reduction in mixtures of hydrogen and inert gases. Alternatively, the metal catalyst may be prepared by synthesizing metal nanoparticle ex situ and supporting said nanoparticles on the basic metal support using a solvent. In some embodiments, the metal catalyst prepared by impregnation (e.g., incipient wetness impregnation) includes at least two metals. In some embodiments, the metal catalyst contains Pd and Cu. In some embodiments, the metal catalyst contains Pd/Cu. For example, the ratio of Pd and Cu can vary, in which Pd may be in molar excess of Cu (e.g., in a 2:1 molar ratio), or Cu may be in molar excess of Pd (e.g., in a 1:2 molar ratio).

The metal catalyst may also be prepared by using the aforementioned methods for supporting metals on basic supports, with the difference that the supports are inert and include $SiO_2$ and carbon. The basic supports are also prepared as mentioned above, but no metal is supported on them. The basic supports and the metal catalysts are physically mixed before the reaction.

The metal catalyst may also be prepared by simultaneous or successive impregnation (e.g., incipient wetness impregnation) of solutions of nitrate or acetate salts of alkali or alkaline earth metals and appropriate salts or complexes of the metals disclosed herein onto inert supports, followed by calcination and reduction in conditions mentioned above. Alternatively, the metal catalyst may be prepared by impregnation (e.g., incipient wetness impregnation) of alkali salts onto inert supports, followed by calcination and impregnation (e.g., incipient wetness impregnation) of ex-situ synthesized metal nanoparticles.

Exemplary Catalysts

The catalyst may include hydrotalcite. In certain embodiments, the catalyst includes hydrotalcite and one or more metals, or two or more metals. The one or more metals, or two or more metals, may include, for example, palladium (Pd), copper (Cu), nickel (Ni), zinc (Zn), ruthenium (Ru), cobalt (Co), and platinum (Pt). The hydrotalcite may be used as part of the catalyst in one or more ways. For example, in one embodiment, the hydrotalcite may include one or more metals deposited by coprecipitation or impregnation (e.g., incipient wetness impregnation). Such examples may include Pd/HT, Cu/HT, and Pd—Cu/HT. In another embodiment, the hydrotalcite may be coprecipitated or impregnated on carbon support (e.g., HT/C), and one or more metals may be coprecipitated or impregnated on such carbon support. Such examples may include Pd/HT/C or Pd—Cu/HT/C. In certain embodiments, the hydrotalcite may be mixed with carbon to produce a support (e.g., HT-C), and one or more metals may be coprecipitated or impregnated on such carbon support. Such examples may include Pd/HT-C or Pd—Cu/HT-C. In yet another embodiment, hydrotalcite may be used alone, or in combination with other catalysts such that the HT is one catalyst out of a mixture of catalysts used. Such an example may include a mixture of catalysts: $Cu/SiO_2$ and Pd/C and HT.

In some embodiments, the catalyst includes: (i) one or more, or two or more, metals such as palladium (Pd), copper (Cu), or a combination thereof; and (i) hydrotalcite. In certain embodiments, the Pd, Cu, or a combination thereof may be coprecipitated or impregnated on the hydrotalcite by methods known in the art. In certain embodiments, the hydrotalcite may be impregnated on carbon support by methods known in the art. In yet other embodiments, the catalyst may further include $TiO_2$. For example, suitable catalysts may include Pd—Cu/HT; Pd—Cu/HT-C; Pd—Cu/HT and $TiO_2$; or Pd—Cu/HT-C and $TiO_2$.

The catalyst may include lanthanum oxide ($La_2O_3$). The $La_2O_3$ may be prepared from any suitable methods known in the art. For example, the $La_2O_3$ may be prepared from the calcination of $La_2(C_2O_4)_3$ or $La_2(NO_3)_3$ at or above 500° C. In certain embodiments, the catalyst includes $La_2O_3$ and one or more metals. The one or more metals may include, for example, palladium (Pd), copper (Cu), nickel (Ni), zinc (Zn), ruthenium (Ru), cobalt (Co), and platinum (Pt). The $La_2O_3$ may be used as part of the catalyst in one or more ways. For example, in one embodiment, the $La_2O_3$ may include one or more metals deposited by coprecipitation or impregnation (e.g., incipient wetness impregnation). In another embodiment, the $La_2O_3$ may be coprecipitated or impregnated on carbon support (e.g., $La_2O_3/C$). In yet another embodiment, the $La_2O_3$ may be used in combination with other catalysts such that the $La_2O_3$ is one catalyst out of a mixture of catalysts used. For instance, the $La_2O_3$ may be used in a mixture with one or more metal-containing catalysts. Such examples may include a mixture of catalysts: $Cu/SiO_2$ and Pd/C and $La_2O_3/C$; or $Cu/ZnO/Al_2O_3$ and Pd/C and $La_2O_3$ and $TiO_2$; or $Cu/ZnO/Al_2O_3$ and $La_2O_3$.

The catalyst may include magnesium oxide (MgO). In certain embodiments, the catalyst includes MgO and one or more metals. The one or more metals may include, for example, palladium (Pd), copper (Cu), nickel (Ni), zinc (Zn), ruthenium (Ru), cobalt (Co), and platinum (Pt). The MgO may be used as part of the catalyst in one or more ways. For example, in one embodiment, the MgO may include one or more metals (including one or more metal oxides) deposited by coprecipitation or impregnation (e.g., incipient wetness impregnation). Such examples may include Cu/MgO, SrO/MgO, or CaO/MgO. In another embodiment, the MgO may be co-precipitated or impregnated on carbon support or silica support. Such examples include MgO/C, and $MgO/SiO_2$. In yet another embodiment, the MgO may be used in combination with other catalysts such that the MgO is one catalyst out of a mixture of catalysts used. For instance, the MgO may be used in a mixture with one or more metal-containing catalysts. Such examples may include a mixture of catalysts: $Cu/ZnO/Al_2O_3$ and $MgO/SiO_2$; or $Cu/ZnO/Al_2O_3$ and SrO/MgO; or $Cu/ZnO/Al_2O_3$ and CaO/MgO; or $Cu/SiO_2$ and CaO/MgO; or PdCu—CaO/MgO; or $Cu/ZnO/Al_2O_3$ and MgO; or $Cu/ZnO/Al_2O_3$, Pd/C and MgO.

The catalyst may include titanium dioxide ($TiO_2$). In certain embodiments, the catalyst includes $TiO_2$ and one or more metals. The one or more metals may include, for example, palladium (Pd), copper (Cu), nickel (Ni), zinc (Zn), ruthenium (Ru), cobalt (Co), and platinum (Pt). The $TiO_2$ may be used as part of the catalyst in one or more ways. For example, in one embodiment, the $TiO_2$ may include one or more metals deposited by coprecipitation or impregnation (e.g., incipient wetness impregnation). In another embodiment, the $TiO_2$ may be co-precipitated or impregnated on carbon support (e.g., $TiO_2/C$). In yet another embodiment, the $TiO_2$ may be used in combination with other catalysts such that the $TiO_2$ is one catalyst out of a mixture of catalysts used. For instance, the $TiO_2$ may be used in a mixture with one or more metal-containing catalysts. Such examples may include a mixture of catalysts: Pd—Cu/HT and $TiO_2$; Pd—Cu/HT-C and $TiO_2$; $Cu/ZnO/Al_2O_3$ and Pd/C and $La_2O_3$ and $TiO_2$; or $Cu/ZnO/Al_2O_3$ and Pd/C and $CeO_2$ and $TiO_2$; or $Cu/ZnO/Al_2O_3$ and Pd/C and MgO and $TiO_2$.

In certain embodiments, the catalyst includes Pd—Cu/HT, Pd—Cu/HT-C, Pd—Cu/HT/C, Pd/HT, Cu/HT, $Cu/ZnO/Al_2O_3$, hydroxyapatite, perovskite, Cu/MgO, $(Cu/ZnO/Al_2O_3)$/HT, $BaO/SiO_2$, $MgO/SiO_2$, $SrO/SiO_2$, $CaO/SiO_2$, SrO/MgO, CaO/MgO, Pd—Cu/NiHT, Cu/NiHT, PdCu/ZnHT, Cu/ZnHT, PdCu/ZnHT, Ru/HT, Cu—Ru/HT, Co/HT, Pt/HT, Pt—Cu/HT, $Cu/SiO_2$, Pd/C, CaO/C, SrO/C, BaO/C, $La_2O_3/C$, $CeO_2/C$, HT/C, HT, $CeO_2$, $La_2O_3$, $TiO_2$, or zeolite. For clarity, it should be understood that "Pd—Cu/HT-C" refers to palladium and copper impregnated on a support of hydrotalcite mixed with carbon, where as "Pd—Cu/HT/C" refers to palladium and copper impregnated on a support of hydrotalcite impregnated on carbon. It should also be understood that any combinations of the catalysts above may be used. In certain embodiments, any combinations of the catalysts above may be used, provided that at least one metal (including, for example, at least one metal oxide) is present in the catalyst.

In one embodiment, the catalyst includes:

Pd—Cu/HT;
Pd—Cu/HT/C;
Pd—Cu/HT and zeolite;
Pd—Cu/HT/C and zeolite;
Pd—Cu/HT and $TiO_2$;
Pd—Cu/HT-C and $TiO_2$;
Pd—Cu/HT/C and $TiO_2$;
Pd/HT;
Cu/HT;
Pd/C and HT
Pd—Cu/C and HT
Pd/HT-C;
Pd/HT/C;
Pd—Cu/HT-C;
$Cu/ZnO/Al_2O_3$ and hydroxyapatite;
$Cu/ZnO/Al_2O_3$ and perovskite;
Cu/MgO;
$Cu/ZnO/Al_2O_3$ and HT;
$Cu/ZnO/Al_2O_3$ and $BaO/SiO_2$;
$Cu/ZnO/Al_2O_3$ and $MgO/SiO_2$;
$Cu/ZnO/Al_2O_3$ and $SrO/SiO_2$;
$Cu/ZnO/Al_2O_3$ and $CaO/SiO_2$;
$Cu/ZnO/Al_2O_3$ and SrO/MgO;
$Cu/ZnO/Al_2O_3$ and CaO/MgO;
$Cu/SiO_2$ and CaO/MgO;
Pd—Cu/CaO—MgO;
Pd—Cu/NiHT;
Cu/NiHT;
Pd—Cu/ZnHT;
Cu/ZnHT;
Ru/HT;
Cu—Ru/HT;
Co/HT;
Pt/HT;
Pt—Cu/HT;
$Cu/SiO_2$, Pd/C and CaO/C;
$Cu/SiO_2$, Pd/C and SrO/C;
$Cu/SiO_2$, Pd/C and BaO/C;
$Cu/SiO_2$, Pd/C and $La_2O_3/C$;
$Cu/SiO_2$, Pd/C and $CeO_2/C$;
$Cu/SiO_2$, Pd/C and HT/C;
$Cu/SiO_2$, Pd/C and HT;
$Cu/ZnO/Al_2O_3$, Pd/C and HT;
$Cu/ZnO/Al_2O_3$ and $CeO_2$;
$Cu/ZnO/Al_2O_3$, Pd/C and $CeO_2$;
$Cu/ZnO/Al_2O_3$ and $La_2O_3$;
$Cu/ZnO/Al_2O_3$, Pd/C and $La_2O_3$;
$Cu/ZnO/Al_2O_3$, Pd/C, $La_2O_3$, and $TiO_2$;
$Cu/ZnO/Al_2O_3$, Pd/C, and $CeO_2$;
$Cu/ZnO/Al_2O_3$, Pd/C, $CeO_2$, and $TiO_2$,
Pd—Cu/ZnO/HT;
Cu/ZnO/HT;
$Cu/ZnO/Al_2O_3$ and MgO;
$Cu/ZnO/Al_2O_3$, Pd/C and MgO; or
$Cu/ZnO/Al_2O_3$, Pd/C, MgO, and $TiO_2$.

It should be understood that the exemplary catalysts described above may be used for any of the methods described herein to produce one or more ketones from compounds of formula (I) and alcohols or aldehydes of formula (II).

e) Solvent and Reaction Conditions

Solvent

Typically, both the intermolecular and the intramolecular reactions described above may be carried out in an aqueous, organic, or biphasic aqueous and organic solvent. In some embodiments, the biphasic aqueous and organic solvent system may give high conversions and high selectivities for particular products. Examples of organic solvents that may be used in either a single component solvent system or a biphasic solvent system include toluene, trimethylacetonitrile, dimethylformamide, propyl-acetate, dioxane, butanol, hexanol, octanol, and any mixture thereof. In some embodiments, the organic solvent used in the biphasic solvent system is an aromatic solvent, such as, for example, toluene.

Reaction Temperature

The operating temperatures used in the methods described herein to produce the one or more ketones may vary. The operating temperature range refers to the range of temperatures across a reaction zone.

In some embodiments, the operating temperature is the reflux temperature of the solvent if one is used. In other embodiments, the reaction mixture containing the compounds of formula (I) and/or formula (II) and the basic catalyst is heated to an operating temperature range suitable to increase selectivity for one or more branched ketones.

The operating temperature range selected may vary depending on various factors, including the solvent and basic catalyst used. In some embodiments, the operating temperature range is between about 25° C. to about 400° C., between about 50° C. to about 350° C., or between about 60° C. to about 200° C.

In some embodiments, in reaction system where a biphasic solvent system such as toluene and water is used as the solvent, the operating temperature range is between about 25° C. to about 250° C., or between about 50° C. to 200° C.

In some embodiments, the reaction may be exothermic and inter-stage cooling may be utilized to maintain the temperature at the operating temperature.

Reaction Time

In some embodiments, the reaction may be carried out for 24 hours, but the time of the reaction will also vary with the reaction conditions (e.g., reaction temperature), catalyst activity, desired yield, and desired conversion (e.g., low conversion with recycle). In some embodiments, the reaction time is determined by the rate of conversion of the starting material or starting materials. In other embodiments, the reaction time is determined by the rate of formation of particular products, such as branched products. In other embodiments, the reaction mixture is heated for 10 to 30 hours. In other embodiments, the reaction mixture is heated for 10 to 20 hours. In yet other embodiments, the reaction mixture is heated for 1 to 10 hours. In yet other embodiments, the reaction mixture is heated for 30 minutes to 10 hours.

Operating Pressure

The operating pressure of the methods described herein to produce the one or more ketones may vary. The operating pressure refers to the pressure across a reaction zone. In some embodiments, the pressure in between 1 atm and 60 atm.

Production of Diesel

The ketones of formula (A) produced by intermolecular reaction between the compounds of formulae (I) and (II) may be suitable for use as diesel precursors. Such ketones can be hydrogenated to yield alkanes suitable for use as diesel.

An exemplary general reaction to produce diesel is:

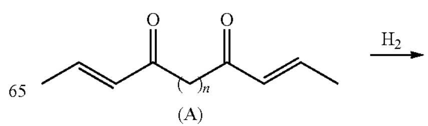

-continued

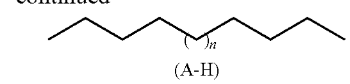

Other exemplary reactions may include, for example:

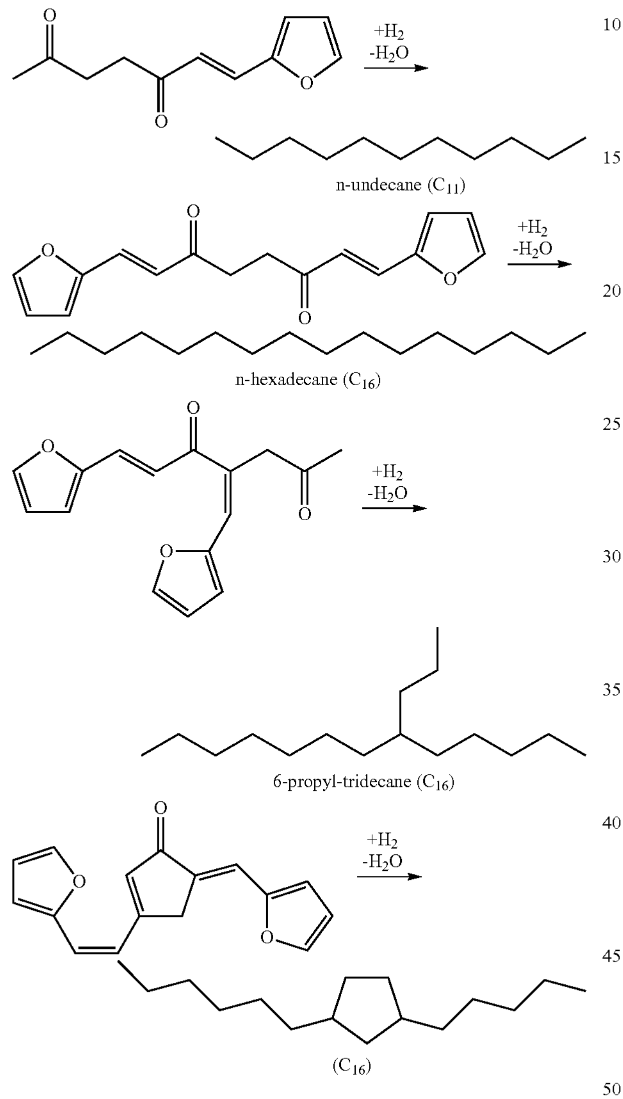

In some embodiments, the compounds of formula (A) can be hydrogenated to yield alkanes with at least six carbon atoms. In certain embodiments, the compounds of formula (A) can be hydrogenated to yield $C_{11}$-$C_{16}$ alkanes. In other embodiments, the compounds of formula (A) can be hydrogenated to yield alkanes with a cetane number of at least 50, at least 60, at least 70, or at least 80. In one embodiment, the alkanes have a cetane number of 83 or 100.

In one embodiment, the alkanes are selected from:

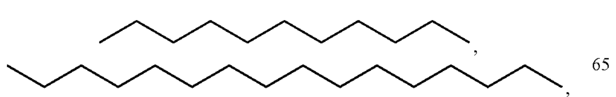

-continued

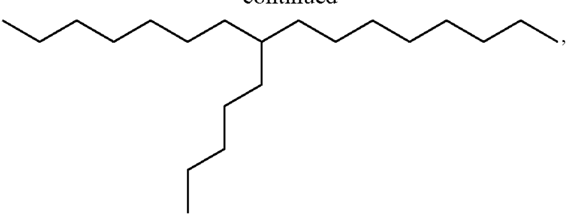

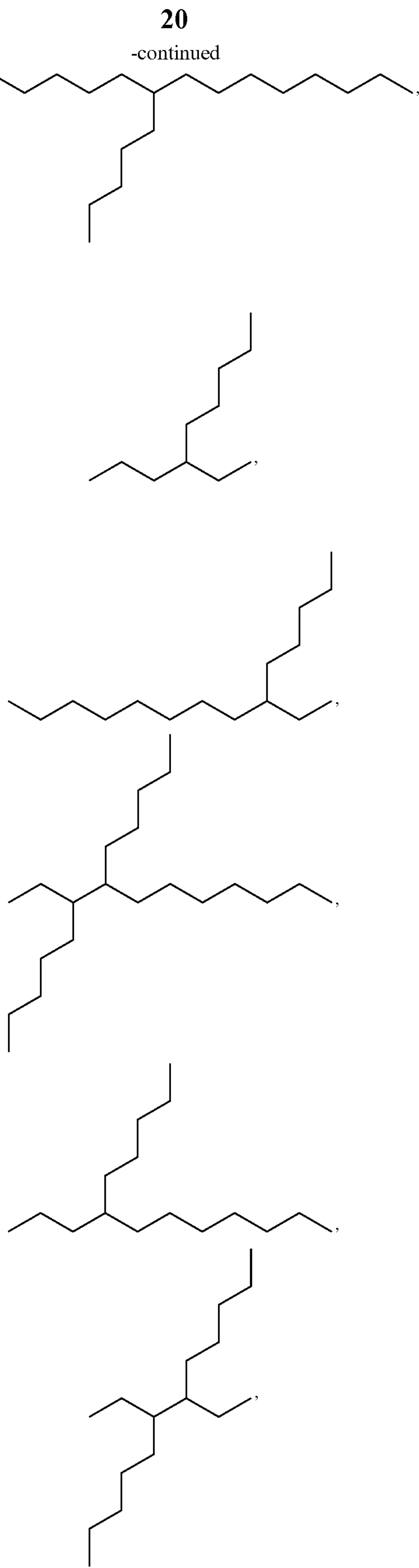

-continued

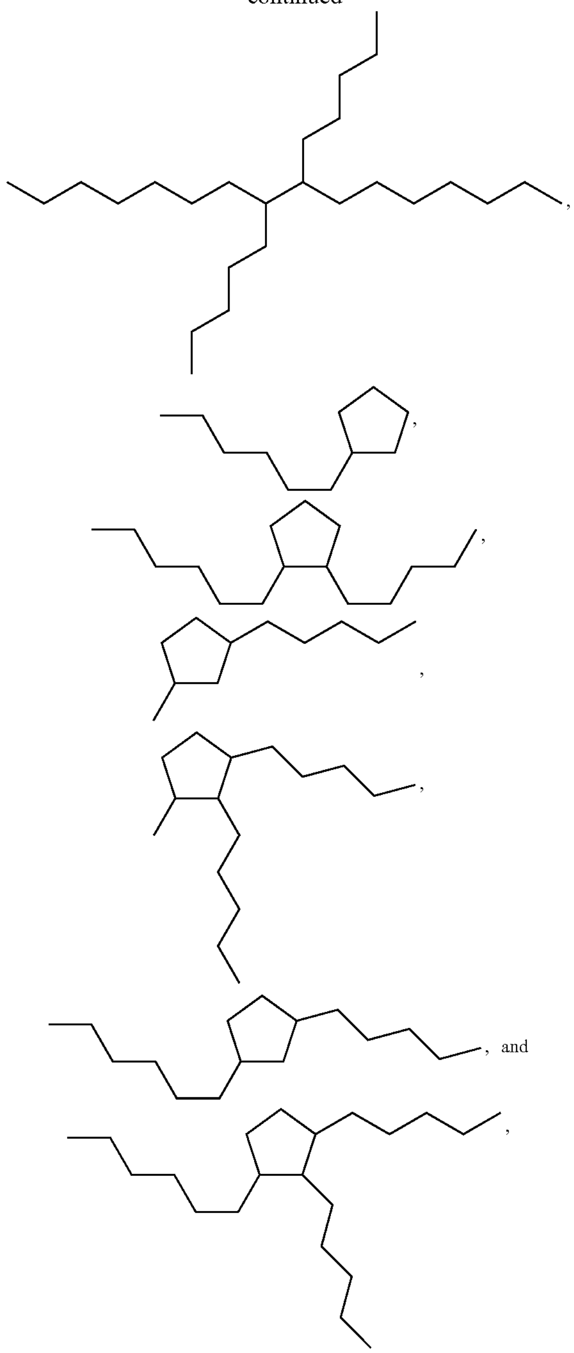

and any mixtures thereof.

The formation of condensation products in which the branched products are formed with hexanedione provides branched alkanes. Branched alkanes reduce the cloud point of the fuel without significant decreases of cetane number.

In some embodiments, the hydrogenation can take place with or without decarbonylation.

Any suitable methods known in the art may be used in hydrogenate compounds of formula (A) to yield alkanes. For example, see He and Wang, *Catalysis for Sustainable Energy,* 2012, 1, 28-52; West, et al., *Catalysis for Sustainable Energy,* 2008, 1, 417-424.

Production of Lubricants a) Ketones and Alcohols to Lubricants

Certain ketones and alcohols may be combined to form lubricant precursors. In some embodiments, the ketone may be a methyl ketone. In one variation, the ketone is acetone. In some embodiments, the alcohol is 2-ethylhexanol:

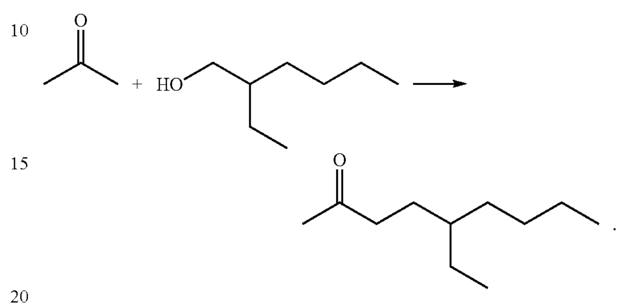

In some embodiments, the ketone formed (such as the $C_{11}$ ketone depicted in the exemplary scheme above) may be hydrogenated and dehydrated to form the alkene (such as a $C_{11}$ alkene). The alkene may then be oligomerized to form alkanes as shown in the following exemplary reaction scheme:

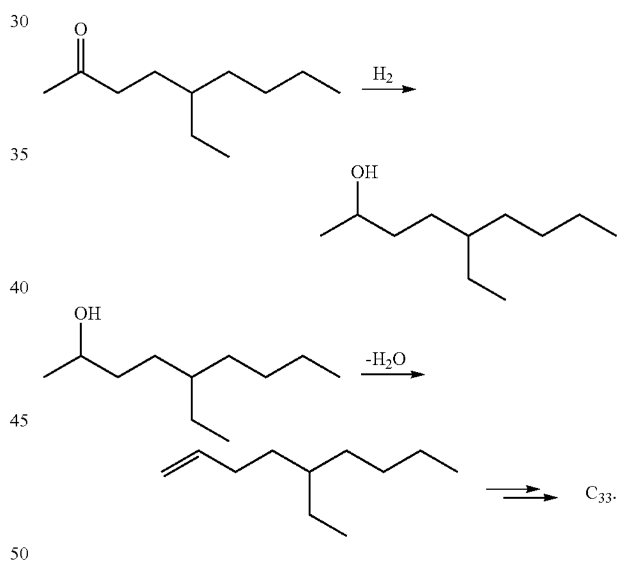

The hydrogenation, dehydration, and oligomerization reactions may be carried out using procedures known in the art. In some embodiments a hydrogenation catalyst comprising one or more metals selected from the group consisting of Cu, Ni, Pt, Pd, Rh, Ru, and Ir may be used in the hydrogenation reaction. In some embodiments, the hydrogenation catalyst is Pd/C, $Pd/Al_2O_3$, Pt/C, $Pt/Al_2O_3$, Ru/C, $Ru/Al_2O_3$, Rh/C, $Rh/Al_2O_3$, or mixtures thereof. In some embodiments, the hydrogenation catalyst is Pd/C or Pt/C.

In some embodiments, the hydrogenation catalyst may also cause decarbonylation.

Provided herein are also methods of producing one or more compounds of formula (IX), by contacting a ketone of formula (VII) with a diol of formula (VIII) to produce the one or more compounds of formula (IX).

The ketone of formula (VII) has the following structure:

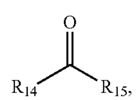

wherein:

$R_{14}$ is alkyl; and $R_{15}$ is H or methyl.

In some embodiments of the ketone of formula (VII), $R_{14}$ is a $C_{1-20}$ alkyl, $C_{1-15}$ alkyl, $C_{1-10}$ alkyl, or $C_{1-5}$ alkyl. In certain embodiments, $R_{14}$ is methyl, ethyl, propyl or butyl. In certain embodiments, $R_{14}$ is H.

The diol of formula (VIII) has the following structure:

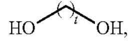

wherein t is an integer greater than or equal to 4.

In some embodiments, t is 4-30, 4-25, 4-20, 4-15, or 4-10. In certain embodiments, the diol of formula (VIII) is hexanediol or heptanediol.

The one or more compounds of formula (IX) have the following structure:

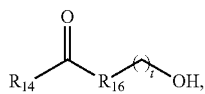

wherein:

$R_{14}$ is as described above for formula (VII)

$R_{16}$ is —$CH_2$—; and t is as described above for formula (VIII).

With reference to the methods of producing one or more compounds of formula (IX), in one exemplary reaction, the ketone is 2-butanone and the diol is 1,6-hexandiol:

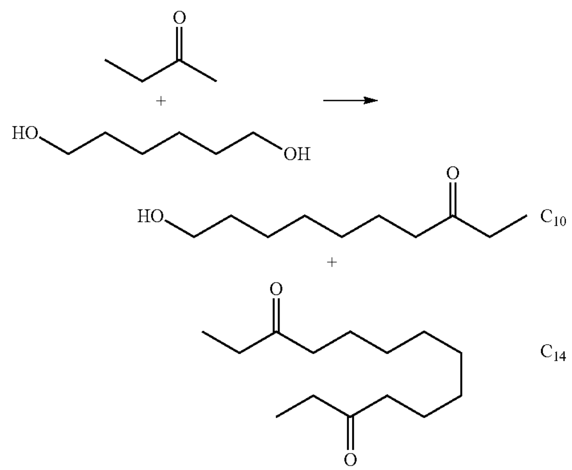

In some embodiments, the reaction is carried out with an excess of the ketone (e.g., 2-butanone, above) such that the $C_{10}$ compound is the main product. This results is unexpected as one of skill in the art would expect that carrying out the reaction with an excess of the alcohol (e.g., 1,6-hexanediol) would lead to the $C_{10}$ compound as the main product. In some embodiments, the $C_{10}$ compound can be hydrogenated and the secondary alcohol preferentially hydrogenated to give 1-decanol using procedures known in the art. In some embodiments, the 1-decanol can be converted to 1-decene which is then oligomerized to $C_{30}$ lubricants using procedures known in the art as shown in the exemplary reaction scheme:

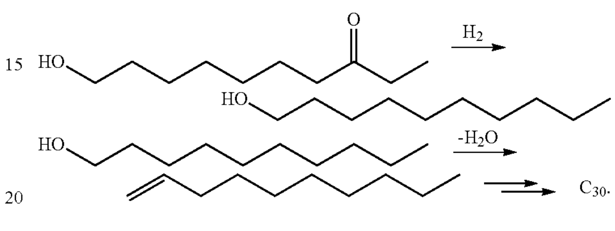

Alternatively, a Guerbet reaction with the $C_{10}$ alcohol and a $C_{12}$-$C_{26}$ alcohol will produce $C_{24}$-$C_{36}$ lubricants as shown in the following exemplary reaction scheme:

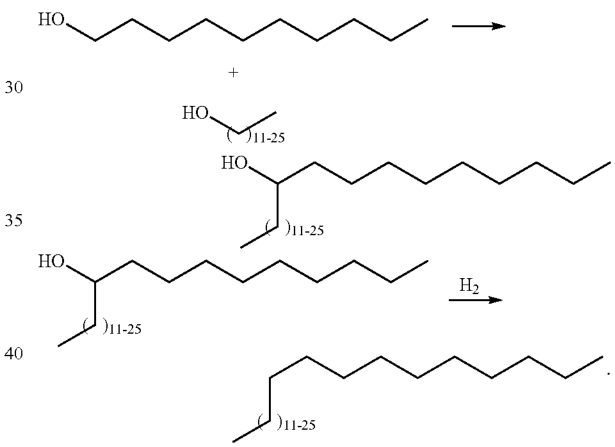

In some embodiments, the ketones of formula (A) or the ketones of formula (C) described above may be reacted with the one or more alcohols to form the lubricants. It will be understood that any combination of ketones and alcohols containing the appropriate number of carbons may be combined to form $C_{24}$-$C_{36}$ lubricants. The Guerbet reaction may be carried out using metal catalyst and optionally base. In some embodiments, the metal catalyst and optionally a base may be the same catalyst and base as the reaction of the ketone with one or more alcohols. In other embodiments, the metal catalyst and optionally a base may be a different catalyst and base as the reaction of the ketone with one or more alcohols.

In some embodiments, a ketone may react with two alcohols to form a higher ketone. The higher ketone is then hydrogenated to an alcohol of formula (C1). The alcohol of formula (C1) is then reacted with one or more alcohols in a Guerbet reaction to form an alcohol of formula (C2). The alcohol of formula (C2) may then be hydrogenated to the $C_{24}$-$C_{36}$ lubricants.

In some embodiments, the hydrogenation can take place with or without decarbonylation.

In some embodiments, the alcohols used in the reaction scheme above will be diols, such as 1,6-hexanediol. It will be understood that in some embodiments, $C_{24}$-$C_{36}$ alkanes may be produced from hydrogenation of alcohol (C1) without the need for subsequent Guerbet reactions depending on the number of carbon atoms present in $R_8$, $R_9$, and $R_{10}$. It will also be understood that in some embodiments, the alcohol (C1) may react with only one additional alcohol instead of two alcohol molecules as shown above. In some embodiments a hydrogenation catalyst comprising one or more metals selected from the group consisting of Cu, Ni, Pt, Pd, Rh, Ru, and Ir may be used in the hydrogenation reaction. In some embodiments, the hydrogenation catalyst is Pd/C, Pd/$Al_2O_3$, Pt/C, Pt/$Al_2O_3$, Ru/C, Ru/$Al_2O_3$, Rh/C, Rh/$Al_2O_3$, or mixtures thereof. In some embodiments, the hydrogenation catalyst is Pd/C or Pt/C.

b) Aldehydes and Alcohols to Lubricants

In some embodiments, an aldehyde may be reacted with one or more alcohols, metal catalyst, and optionally base to form lubricant precursors which may then be converted to lubricants. In some embodiments, the lubricants formed are in the $C_{24}$-$C_{36}$ range. In some embodiments, an aldehyde of formula (V) may be reacted with one or more alcohols of formula (VI), metal catalyst, and optionally base to form one or more lubricant precursors of formula (E) according to the following exemplary reaction scheme:

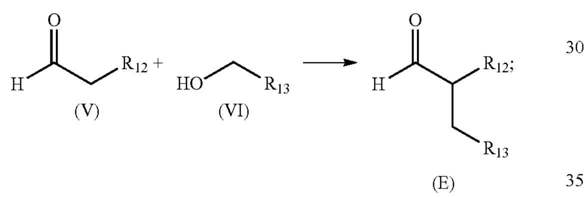

wherein each $R_{12}$ and $R_{13}$ is independently selected from the group consisting of alkyl, aryl, alkenyl, alkynyl, and heteroaryl.

In some embodiments, each $R_{12}$ and $R_{13}$ is independently selected from the group consisting of $C_1$-$C_{20}$ alkyl, $C_6$-$C_{20}$ aryl, $C_2$-$C_{20}$ alkenyl, $C_2$-$C_{20}$ alkynyl, and $C_4$-$C_{21}$ heteroaryl. In certain embodiments, each $R_{12}$ and $R_{13}$ is independently selected from the group consisting of $C_1$-$C_{10}$ alkyl, $C_6$-$C_{20}$ aryl, $C_2$-$C_{10}$ alkenyl, $C_2$-$C_{10}$ alkynyl, and $C_4$-$C_{21}$ heteroaryl.

In some embodiments, the alcohol is a diol such as 1,6-hexanediol as shown in the following exemplary reaction with acetaldehyde:

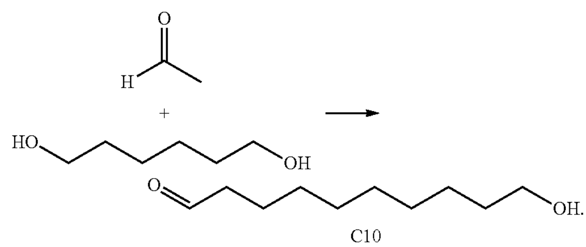

It will be understood that a variety of products may be formed due to competing self aldol-condensation reactions with the aldehyde and the alkylation reaction with the alcohol. For example, products formed in the exemplary reaction of 1,6-hexanediol with butyraldehyde may include the following:

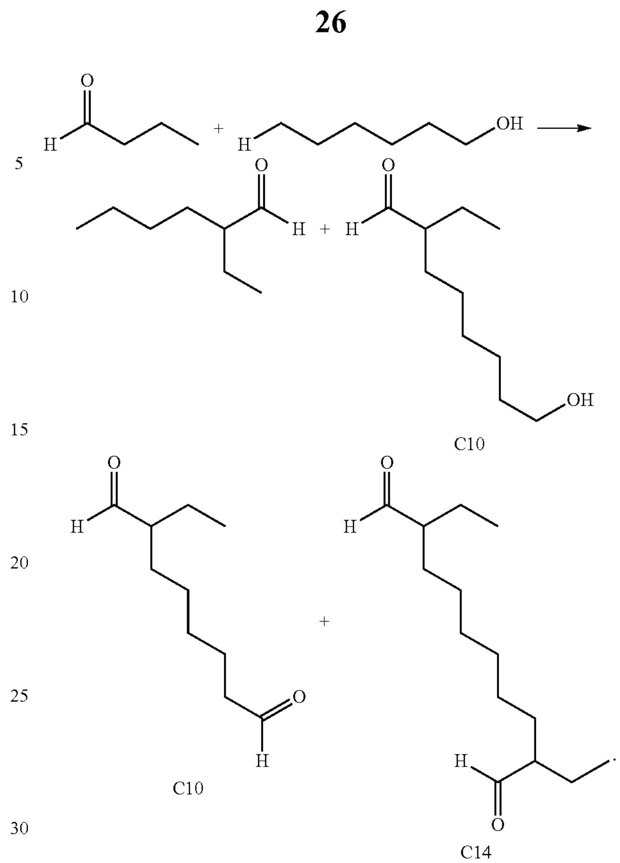

In some embodiments, the $C_{10}$ aldehyde formed can be hydrogenated to 1,10-decanediol. In other embodiments, the 1,10-decanediol may be hydrogenated to 1-decanol. In some embodiments a hydrogenation catalyst comprising one or more metals selected from the group consisting of Cu, Ni, Pt, Pd, Rh, Ru, and Ir may be used in the hydrogenation reaction. In some embodiments, the hydrogenation catalyst is Pd/C, Pd/$Al_2O_3$, Pt/C, Pt/$Al_2O_3$, Ru/C, Ru/$Al_2O_3$, Rh/C, Rh/$Al_2O_3$, or mixtures thereof. In some embodiments, the hydrogenation catalyst is Pd/C or Pt/C. In some embodiments, the 1-decanol can be converted to 1-decene which is then converted to $C_{30}$ lubricants by processes that are known in the art. In other embodiments, the 1-decanol can be reacted with one or more alcohols in a Guerbet reaction to form $C_{24}$-$C_{36}$ alcohols that are converted to the $C_{24}$-$C_{36}$ lubricants. The Guerbet reaction may be carried out using metal catalyst and optionally base. The metal catalyst and optionally a base may be the same catalyst and base as the reaction of the ketone or aldehyde with one or more alcohols.

In some embodiments, the $C_{10}$ aldehyde may be decarbonylated to form a $C_9$ alcohol. The $C_9$ alcohol is then either converted to an alkene and oligomerized to form a $C_{27}$ alkane, or the $C_9$ alcohol may undergo self Guerbet chemistry followed by hydrogenation to form a $C_{27}$ alkane.

c) Reaction Conditions for Lubricant Production

The Metal Catalyst

Certain metal catalysts that can catalyze the reaction of the ketone or aldehydes with one or more alcohols may be employed in the methods described herein. Certain metal catalysts that can catalyze the Guerbet reaction may be employed in the methods described herein. The metal catalysts that can catalyze the reaction of the ketone or aldehydes with the one or more alcohols and the metal catalysts that can catalyze the Guerbet reaction may be the same or different. In some embodiments, the metal catalyst that catalyzes the reaction of the ketone or aldehydes with one or more alcohols and the metal catalyst that catalyzes the Guerbet reaction are the same, such as for example, Pd/C or Pt/C. In some embodiments, the metal catalyst that catalyzes the reaction of the ketone or aldehydes with one or more alcohols and the metal catalyst that catalyzes the Guerbet reaction are different. It will be understood that even if the catalysts are the same, the base, the solvent, the temperature, the reaction time, and all other possible reaction variables may need to be optimized to obtain the highest yields and highest selectivities for the desired product (e.g., the higher ketones, higher aldehydes, or Guerbet products).

In some embodiments, the metal catalyst includes a transition metal. In some embodiments, the metal-based catalyst includes a late transition metal. In some embodiments, the metal catalyst includes a metal selected from the group consisting of ruthenium, iron, palladium, platinum, cobalt, and copper. Mixtures of these metals are also contemplated, including for example metal alloys. In some preferred embodiments, the metal is palladium.

In other embodiments, the metal catalyst may include transition metals such as nickel, ruthenium, rhodium, palladium, rhenium, iridium, or platinum. In other embodiments, the metal catalyst includes palladium or platinum. In certain embodiments, the metal catalyst is $[Ir(COD)Cl]_2$, $RuCl_2(COD)$, $PtCl_2(COD)$, $[Rh(COD)Cl]_2$, Ni/Si-Alumina, Ru/C, Rh/C, Pt/C, or Pd/C.

In some embodiments, the metal catalyst is a single component metal oxide, an alkaline earth metal oxide, or a rare earth oxide (e.g., $ThO_2$, $ZrO_2$, ZnO, $TiO_2$).

In yet other embodiments, the metal catalyst is a palladium-based catalyst. Palladium-based catalysts may include palladium metal, and complexes of suitable ligands including those containing P and/or N atoms for coordinating to the palladium atoms, and other simple palladium salts either in the presence or absence of ligands. Palladium-based catalysts may also include palladium and palladium complexes supported or tethered on solid supports, such as palladium on carbon (Pd/C), as well as palladium black, palladium clusters, or palladium clusters containing other metals. Suitable examples of palladium-based catalysts may include $Pd(OAc)_2$, $Pd_2(dba)_3$, $Pd(OH)_2/C$, Pd/C, $Pd/CaCO_3$, Pd/Alumina, and Pd-polyethylenimines on silica.

Catalyst Support

In some embodiments, the metal catalyst may be a solid-supported metal catalyst. A solid-supported metal catalyst used herein typically is a metal catalyst where the metal is deposited or impregnated onto a support.

In some embodiments, the support is selected from the group consisting of hydrotalcite, single component metal oxides, alkaline earth oxides, alkali metal oxides, rare earth oxides, $ThO_2$, MgO, Na doped MgO, SrO, BaO, CaO, ZnO, $La_2O_3$, $TiO_2$, $ZrO_2$, $Al_2O_3$, hydroxyapatite, fluorapatite, tert-butoxyapatite, sepiolite, basic zeolites, alkali ion-exchanged zeolites, alkali ion-added zeolites, Pd/NaY zeolite, $Pd/NH_4$-β zeolite, supported alkali metal ions, alkali metal ions on alumina, alkali metal ions on silica, alkali metal on alkaline earth oxide, alkali metals and alkali metal hydroxides on alumina, $Metal/SiO_2$, $Na/SiO_2Pd/Na/SiO_2$, $Na/Ca/SiO_2$, $Na/Ca/SiO_2$, $Cs/SiO_2$, metal-supported zeolite, potassium oxide supported on zeolite Y, synthetic chrysotiles, $Mg_3(OH)_4Si_4O_5$, cobalt(II)-substituted chrysotile, amino-functionalized mesoporous silica, amino-functionalized MCM-41, alkali ion-exchanged mesoporous silica, alkali ion-exchanged SBA-15, ionic liquid supported MgO, amorphous aluminophosphate, synthetic talcs, magnesium organo silicates, KF supported on alumina, lanthanide imide on zeolite, and lanthanide nitride on zeolite. In some embodiments, the support is an alkali exchanged zeolite such as NaY, KY, RbY, CsY, NaX, KX, RbX, and CsX. In some embodiments, a metal such as Pd or Cu is deposited on the alkali exchanged zeolite and used as the metal based catalyst such as, for example, Pd/CsY and Cu/CsY. In some embodiments, alkali metal ions are added to the support (e g, alkali metal ions on alumina, alkali metal ions on silica, alkali metal on alkaline earth oxide, alkali metals and alkali metal hydroxides on alumina).

In some embodiments, the support is a hydrotalcite or a material derived from a hydrotalcite. In some embodiments, the hydrotalcite or material derived from a hydrotalcite comprises one or more metals selected from the group consisting of magnesium, aluminum, lithium, zinc, copper, and nickel. In some embodiments, the hydrotalcite or material derived from a hydrotalcite comprises one or more metals selected from the group consisting of Mg, Al, Li, Zn, Cu, and Ni. Basicity of hydrotalcites can be tuned by varying the magnesium-aluminum ratio, by rehydrating calcined hydrotalcite, or doping the hydrotalcite with Na and K. In some embodiments, hydrotalcites are prepared by co-precipitation of alkaline earth metal salts and/or aluminum nitrates in a solution that includes urea or ammonia and ammonium carbonate or potassium hydroxide and potassium carbonate or sodium hydroxide and sodium carbonate. In some embodiments, alkaline earth metal supports might be prepared by decomposition of nitrate, carbonate or dicarboxylic acid salts at elevated temperatures, from 450° C. to 900° C.

Basic Catalysts

In some embodiments, the catalysts include one or more metals, and a basic support.

Catalyst basicity may be measured by a variety of techniques known to one of skill in the art. For example, basicity of the catalyst can be measured by $CO_2$ temperature-programmed desorption (TPD). In some embodiments, the $CO_2$ TPD is carried out by adsorbing $CO_2$ to the catalyst at room temperature and heating up to 773 K (or similar assay). In some embodiments, for non-zeolite catalysts, preferred catalysts have base site densities measured by $CO_2$ TPD of at least 50 micromoles/gram of catalyst. In other embodiments, for zeolite catalysts, preferred catalysts have base site densities by $CO_2$ TPD of at least 10 micromoles/gram of catalyst. In other embodiments, all preferred catalysts of all types have base site densities by $CO_2$ TPD of at least 10 micromoles/gram of catalyst.

Basicity of the catalyst may also be measured using zero charge determination (Regalbuto), or using the Hammett indicator method.

In some embodiments, the metal catalysts have a pKa from 10 to 16. In other embodiments, the metal catalysts have a pKa from 11 to 15. In some embodiments, the metal catalysts has a $CO_2$ desorption of at least 200° C. Quantitative determination of the pKa and other methods to characterize the basicity of a catalyst support such as hydrotalcite are known in the art. See, e.g., A. Corma, et al., *J. of Catalysis,* 1992, 134, 58 and D. Debecker, et al., *Chem. Eur. J.,* 2009, 15, 3920.

It should be understood that the metal catalyst can be prepared by any method known to one of skill in the art. For example, incipient wetness impregnation is one exemplary technique that can be used. In one example, a support such as hydrotalcite, and metal salt such as palladium chloride or copper acetate can be combined and a solvent such as water is added. The metal salt and support are allowed to react for a period of time between 1 and 24 hours at a temperature between room temperature and 200° C., or more specifically between 50 and 120° C. The reaction mixture may be stirred under a hydrogen atmosphere. The solid catalyst is then filtered and washed with copious amounts of solvent. The solid may then be dried under vacuum at a temperature between 80 and 150° C. Optionally, other additives may be added to the reaction mixture such as alkali metal salts (e.g., sodium chloride or potassium chloride) or a base as described above.

The metal catalyst may also be prepared by incipient wetness impregnation of metal salts on basic supports, followed by calcination at temperatures higher than 300° C. in air or inert gases and/or reduction in mixtures of hydrogen and inert gases. Alternatively, the metal catalyst may be prepared by synthesizing metal nanoparticles ex situ and supporting said nanoparticles on the basic metal support using a solvent. In some embodiments, the metal catalyst prepared by incipient wetness impregnation includes at least two metals.

The metal catalyst may also be prepared by using the aforementioned methods for supporting metals on basic supports, with the difference that the supports are inert and include $SiO_2$ and carbon. The basic supports are also prepared as mentioned above, but no metal is supported on them. The basic supports and the metal catalysts are physically mixed before the reaction.

The metal catalyst may also be prepared by simultaneous or successive incipient wetness impregnation of solutions of nitrate or acetate salts of alkali or alkaline earth metals and appropriate salts or complexes of the metals disclosed herein onto inert supports, followed by calcination and reduction in conditions mentioned above. Alternatively, the metal catalyst may be prepared by incipient wetness impregnation of alkali salts onto inert supports, followed by calcination and incipient wetness impregnation of ex-situ synthesized metal nanoparticles.

Base

In some embodiments, a base is used in combination with the metal catalyst to convert the ketone or aldehyde and one or more alcohols to one or more higher ketones or higher aldehydes (e.g., lubricant precursors) which are then hydrogenated to form lubricants. It should be understood that, in certain embodiments, even when the metal catalyst has a basic support, base may additionally be added to the reaction mixture.

Bases that promotes alkylation of the ketone or aldehyde with one or more alcohols may be used. In certain preferred embodiments, the base is $K_3PO_4$. In some embodiments, the base and metal catalyst are two separate components that may be combined and contacted with the reactants. In other embodiments, the base is first supported or impregnated on a support material typically containing the metal catalyst and contacted with the reactants.

Suitable bases may include inorganic bases (e.g., hydroxides of alkali metals and alkaline earth metals), and organic bases. Examples of inorganic bases may include potassium hydroxide, barium hydroxide, cesium hydroxide, sodium hydroxide, strontium hydroxide, calcium hydroxide, lithium hydroxide, rubidium hydroxide, and magnesium hydroxide. Examples of organic bases may include triethylamine, trimethylamine, pyridine, and methyl amine.

In some embodiments, the base has a pKa from 10 to 16. In other embodiments, the base has a pKa from 11 to 15. In certain embodiments, the base is KOH, $Ba(OH)_2.8H_2O$, $K_2CO_3$, KOAc, $KH_2PO_4$, $Na_2HPO_4$, pyridine, or $Et_3N$.

The type of base used may be determined by the desired strength of the base and its ability to promote alkylation of a ketone or aldehyde, without producing undesirable side reactions or side products. The amount of base selected may affect the overall reaction yield, and the proportion of alkylated products. In certain embodiments, the type of base used may be determined by the desired strength of the base and its ability to promote alkylation of the ketone or aldehyde, without producing undesirable side reactions or side products. The amount of base selected may affect the overall reaction yield.

In yet other embodiments, the base used may be calcined. In such embodiments, the base can be pretreated at a high temperature to obtain a more active material. For example, in one embodiment where $K_3PO_4$ is the base used, the $K_3PO_4$ may be heated at about 600° C. to obtain a material that is more active in promoting the alkylation reaction described herein.

Solvent

In some embodiments, the methods of producing the lubricant precursors are performed neat, i.e., without addition of a solvent. However, in other embodiments, the methods of producing the lubricant precursors may be performed with a solvent.

Any solvent that promotes alkylation of the ketone or aldehyde may be employed in the process described herein. For example, the solvent may be an organic solvent. Organic solvents may include aromatics (e.g., toluene, benzene), ketones (e.g., acetone or methyl ethyl ketone), acetates (e.g., ethyl acetate or isopropylacetate), nitriles (e.g., acetonitrile), alcohols (e.g., butanol, ethanol, isopropanol), or ethers (e.g., diglyme, monoglyme, diglybu, THF). As used herein, "diglyme" refers to diethylene glycol dimethyl ether. As used herein, "diglybu" refers to diethylene glycol dibutyl ether.

Operating Temperature

The operating temperatures used in the methods described herein to produce the lubricant precursors may vary. The operating temperature range refers to the range of temperatures across a reaction zone. In some embodiments, the operating temperature is the reflux temperature of the solvent if one is used. The operating temperature range selected may vary depending on various factors, including the solvent, base, and catalyst used. In some embodiments, the operating temperature range is between about 100° C. to about 400° C., between about 190° C. to about 350° C., or between about 220° C. to about 270° C.

In some embodiments, in reaction system where toluene is used as the solvent, the operating temperature range is between about 110° C. to about 250° C., or between about 180° C. to 250° C.

In some embodiments, the reaction may be exothermic and inter-stage cooling may be utilized to maintain the temperature at the operating temperature.

Operating Pressure

The operating pressure of the methods described herein to produce the hydrocarbon ketones may vary. The operating pressure refers to the pressure across a reaction zone. In some embodiments, the pressure in between 1 atm and 60 atm.

Reaction Time

In some embodiments, the reaction may be carried out for 24 hours, but the time of the reaction will also vary with the reaction conditions (e.g., reaction temperature), catalyst activity, desired yield, and desired conversion (e.g., low conversion with recycle). In some embodiments, the reaction time is determined by the rate of conversion of the starting material. In other embodiments, the reaction mixture is heated for 10 to 30 hours. In other embodiments, the reaction mixture is heated for 10 to 20 hours. In yet other embodiments, the reaction mixture is heated for 1 to 10 hours. In yet other embodiments, the reaction mixture is heated for 30 minutes to 10 hours.

d) Other Routes to Lubricants

Other exemplary reactions to produce lubricants may include, for example:

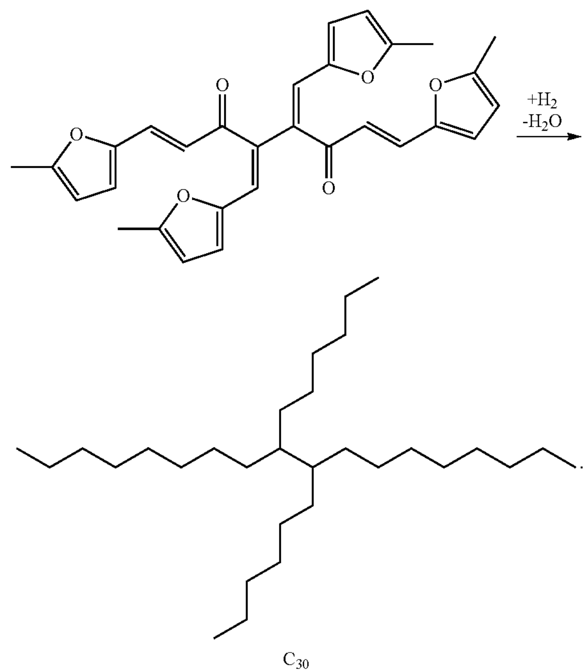

The hydrogenation reaction may be carried out by processes known in the art. In some embodiments, the hydrogenation can take place with or without decarbonylation.

In some embodiments a hydrogenation catalyst comprising one or more metals selected from the group consisting of Cu, Ni, Pt, Pd, Rh, Ru, and Ir may be used in the hydrogenation reaction. In some embodiments, the hydrogenation catalyst is Pd/C, Pd/$Al_2O_3$, Pt/C, Pt/$Al_2O_3$, Ru/C, Ru/$Al_2O_3$, Rh/C, Rh/$Al_2O_3$, or mixtures thereof. In some embodiments, the hydrogenation catalyst is Pd/C or Pt/C.

Production of Gasoline Additives

The ketones of formula (B) produced by intramolecular reaction of the compounds of formula (I) may be suitable for use as gasoline precursors. Such ketones can be hydrogenated to yield cycloalkanes suitable for use as gasoline additives.

An exemplary reaction to produce gasoline additives is:

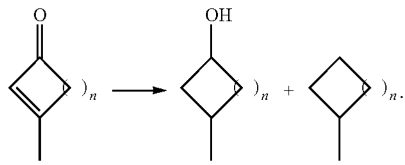

In one embodiment, the gasoline additives are

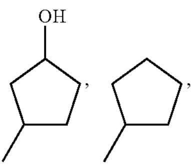

or any mixtures thereof.

Any suitable methods known in the art may be used for hydrogenation to yield cycloalkanes (optionally substituted by —OH) suitable for use as gasoline additives. In some embodiments a hydrogenation catalyst comprising one or more metals selected from the group consisting of Cu, Ni, Pt, Pd, Rh, Ru, and Ir may be used in the hydrogenation reaction. In some embodiments, the hydrogenation catalyst is Pd/C, Pd/$Al_2O_3$, Pt/C, Pt/$Al_2O_3$, Ru/C, Ru/$Al_2O_3$, Rh/C, Rh/$Al_2O_3$, or mixtures thereof. In some embodiments, the hydrogenation catalyst is Pd/C or Pt/C.

As used herein, the term "about" refers to an approximation of a stated value within an acceptable range. Preferably, the range is +/−10% of the stated value.

EXAMPLES

The following Examples are merely illustrative and are not meant to limit any aspects of the present disclosure in any way.

Example 1

Hydrotalcite Material Calcination and Characterization

A Pyrex dish was weighed at 180.82 g prior to addition of synthetic hydrotalcite ($CH_{16}Al_2Mg_6O_{19}.4H_2O$; Aldrich: 652288-1 kg). Approximately 100.59 g of hydrotalcite was added to the dish prior to calcination in the first floor static air calcinations furnace. The calcination was programmed for 2° C./min up to 700° C. and held for 2 hours at temperature. The material was then cooled in the furnace and removed after cooling to RT. After cooling, 56.50 g of material was recovered. The calcined material is $Mg_6Al_2O_9$ (MW 343.76). Therefore, the theoretical recovery would be 56.94 g assuming complete transfer.

Example 2

Temperature Programmed Desorption (TPD) of $CO_2$ on 600° C. Hydrotalcite-Derived Material 200.0 mg of synthetic hydrotalcite ($CH_{16}Al_2Mg_6O_{19}.4H_2O$; Aldrich: 652288-1 kg) that had been calcined at 600° C. (2° C./min) and held for 1 hour was measured out. The material was heated to the calcination temperature at 2° C./min (profile 4) under 10.0 mL/min He flow (12.5 psi at injector) with venting to atmosphere. The material was held at the calcination temperature for 1 hour and then cooled. $CO_2$ was then adsorbed by setting the temperature of the furnace to 50° C. and the bottom valve to vent to atmosphere. $CO_2$ was flowed over the catalyst bed (approx. 200 mg) at 40 mL/min (rotameter set point—57) for 1 hour. The $CO_2$ flow was then switched back to He. The material was then heated to 100° C. at 10° C./min under 18.3 mL/min He flow (20 psi at injector). The material was held at temperature for 1 hour. The TPD was measured by adding a Drierite® column to the bottom of the reactor. The TPD method was loaded (1050° C. TPD) and a single sample was injected. The furnace temperature program began at 0° C. and heated at 10° C./min to 1050° C. The temperature was held for 30 minutes at 1050° C. The furnace was then cooled. After completion of TPD, the mass of recoverable material was 185.0 mg with some material remaining in the tube. This indicates the material had low initial moisture or carbon uptake. The results are summarized in Table 1 below.

TABLE 1

| Calcination Temperature (° C.) | Surface Area ($m^2/g$) | $CO_2$ TPD Results (μmol/g) |
|---|---|---|
| 450 | 218.0 | 212 |
| 500 | 235.5 | 216 |
| 550 | 233.2 | 180 |
| 600 | 224.3 | 152 |
| 650 | 214.8 | 125 |
| 700 | 193.4 | 102 |
| 700 - 2 hr hold | 182.0 | 100 |

Example 3

Synthesis of MgZrO Catalyst from Magnesium Nitrate and Zirconyl Oxychloride

1 L nanopure water was added to a 1 L Erlenmeyer flask. 50.9003 g magnesium nitrate hexahydrate and 5.8517 g zirconyl oxychloride octahydrate was added to the 1 L nanopure water. The solution was stirred and then transferred to a 2 L beaker. A 900 mL 1M NaOH solution was prepared by adding 35.9973 g NaOH pellets to 900 mL nanopure water in a 1000 mL pyrex bottle. The 1M NaOH solution was added by pipet to the $MgO/ZrO_2$ solution with stirring until the pH reached 10. The initial pH of the solution was 1.81, and 400 mL of 1M NaOH was added in order to reach pH 10. A white, cloudy gel formed (rpm 600) which was stirred for 2 hours. The material was left to stand without stirring for an additional 70 hours to age. The gel formation began immediately upon addition of NaOH to the $MgO/ZrO_2$ solution.

The above procedure was repeated in a second reaction. In this reaction white powder was largely separated into aqueous and solid layer upon addition of NaOH to the $MgO/ZrO_2$ solution. The aqueous layer was removed. The solid layer was initially filtered; however, filtration was extremely slow due to plugging of the filter and the thickness of the gel. The solid/liquid layer was transferred into fourteen, 50 mL centrifuge tubes. The tubes were centrifuged at 4000 RPM for 5 minutes to yield a clean separation between phases. Approximately 10 mL of solid was collected from each of the tubes and the 40 mL aqueous layer was poured off and collected. Each tube had fresh millipure water added to 50 mL and was stirred manually with a micro-spatula to get a good dispersion. The tubes were then shaken and centrifuged again. Again, 10 mL of solid was recovered from each tube. Addition of water followed by centrifugation was repeated. After this repeat, approximately 5 mL of solid remained in each tube. Centrifugation for 5 minutes produced a dispersion of the solid in the liquid phase and a solid pellet. The combined liquid layer was collected and left overnight. The pH of the mixture remained near 10.

The combined liquid layer from the previous day was re-centrifuged in 12 centrifuge tubes for 15 minutes yielding a clean separation. Each tube contained approximately 3 mL of solid. The removed liquid layer from the re-centrifuged material was filtered through a 0.22 μm polyethersulfone filter yielding a clear liquid layer. The small layer of solid was collected and combined with the remaining solids. The combined solids from the original 14 tubes were combined into 3 tubes with a micro-spatula. Complete transfer was ensured with two 5-10 mL washings of each tube with millipure water. The solids from the 12 re-centrifuged tubes were combined in the same way into one tube. The solid volume from the four combined centrifuge tubes was approximately 40 mL total solids. The combined tubes were centrifuged for 25 minutes at 4000 RPM yielding good phase separation. The material was then filtered through a 0.22 μm polyethersulfone filter yielding a clear liquid. The tubes were rinsed three times with 10 mL of water to ensure a good transfer. The material was rinsed a final time with 150 mL of millipure water to remove any remaining NaOH. The pH of the final washing was 9.73. A sample of the liquid layer was stored in a 20 mL scintillation vial. The solid was transferred after vacuum filtration was complete into a pyrex dish weighing 180.82 g. The added solids weighed approximately 39.8 g. The solid was then put into a muffle furnace at 120° C. and dried for 24 hours. After drying, 12.25 g of solid was recovered. Approximately 100 mg of this dried material was stored for further testing. The remaining solid was then covered with parafilm and stored for calcination.

The dried material was placed in a Pyrex dish and heated to 873 K in a 3 hour ramp and held at temperature for 3 hours in air. It was then cooled to ~50° C. under natural convective cooling and retrieved 14 hours after calcinations began. The solid material was then finely ground in a mortar and pestle. After collecting the finely ground material, a total of 9.244 g of material was collected and placed in an amber bottle and sealed with parafilm for subsequent use.

Example 4

Aldol Condensation of 2,5-Hexanedione at 25° C. and 50° C.

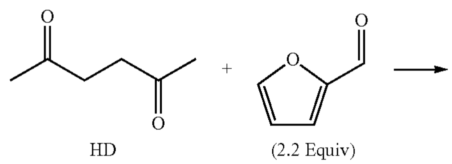

-continued

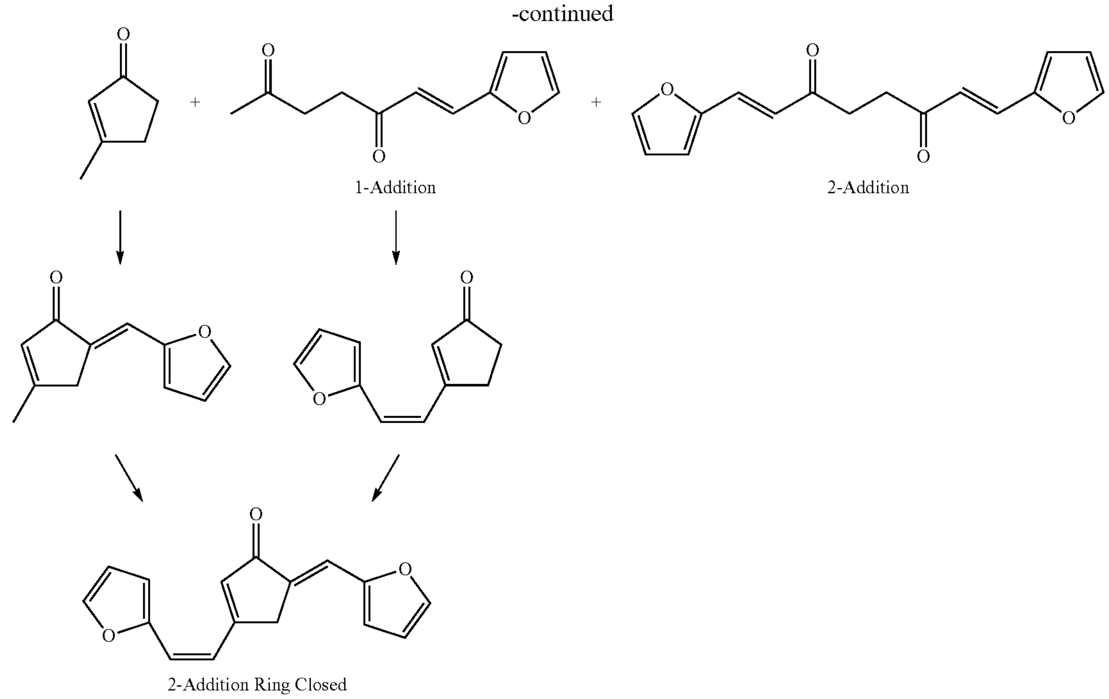

Toluene (Fisher), 2,5-hexanedione (Aldrich), dodecane (Aldrich), and furfural (Aldrich) were used as received. MgAlO was calcined as described in Example 1. A mixture of 3.277 g furfural, 1.123 g DD, 1.769 g 2,5-hexanedione, and 22.62 g toluene was prepared in a small beaker. A portion of this mixture, water, and the basic catalyst were added to a scintillation vial as set forth in Table 2 below.

TABLE 2

| Reactor | Amt. Mixture (g) | Amt Water (g) | Base Amount (mg) | Reaction Time (hr) | Temp (° C.) |
|---|---|---|---|---|---|
| 1 | 2.215 g | 2.00 g | 50.0 MgAlO | 24 | 25 |
| 2 | 2.215 g | 2.00 g | 100.0 MgAlO | 24 | 25 |
| 3 | 2.215 g | 2.00 g | 200.0 MgAlO | 24 | 25 |
| 4 | 2.215 g | 2.00 g | 25.0 μL of 2M NaOH | 24 | 25 |
| 5 | 2.215 g | 2.00 g | 200.0 μL of 2M NaOH | 24 | 25 |
| 6 | 1.107 g + 0.870 g fresh Toluene | 2.00 g | 100.0 MgAlO | 24 | 25 |
| 7 | 2.215 g | 2.00 g | 50.0 MgAlO | 24 | 50 |

TABLE 2-continued

| Reactor | Amt. Mixture (g) | Amt Water (g) | Base Amount (mg) | Reaction Time (hr) | Temp (° C.) |
|---|---|---|---|---|---|
| 8 | 2.215 g | 2.00 g | 100.0 MgAlO | 24 | 50 |
| 9 | 2.215 g | 2.00 g | 200.0 MgAlO | 24 | 50 |
| 10 | 2.215 g | 2.00 g | 25.0 μL of 2M NaOH | 24 | 50 |
| 11 | 2.215 g | 2.00 g | 200.0 μL of 2M NaOH | 24 | 50 |
| 12 | 1.107 g + 0.870 g fresh Toluene | 2.00 g | 100.0 MgAlO | 24 | 50 |

The reactors were placed on pre-heated stir plates and stirred at 800 RPM. For each reactor, all material was transferred to a 15 mL centrifuge tube and centrifuged at 4000 RPM. The organic layer was collected in a second 15 mL centrifuge tube. The aqueous phase was washed 3 more times with 4 mL of EtOAc and centrifuged. The organic fractions were combined and dried over $Na_2SO_4$. A sample from the organic layer was analyzed by GC. The results are summarized in Table 3 below.

TABLE 3

| Catalyst | HD Conv. (%) | Furfural Conv. (%) | MCP Yield (%) | 1-Add. Yield (%) | 2-Add. Yield (%) | 2-Add-Ring Closed (%) | Product Sum (%) |
|---|---|---|---|---|---|---|---|
| 50 mg AlMgO | 77.2 | 50.8 | 0.5 | 46.9 | 4.4 | 0.2 | 51.6 |
| 100 mg AlMgO | 91.3 | 65.8 | 0.5 | 48.8 | 7.9 | 0.5 | 57.2 |
| 200 mg AlMgO | 99.8 | 91.5 | 0.4 | 31.2 | 17.6 | 0.8 | 49.5 |
| 25 μL 2M NaOH | 68.0 | 40.3 | 0.6 | 47.5 | 1.2 | 0.1 | 48.8 |
| 200 μL 2M NaOH | 100.0 | 90.6 | 0.5 | 22.2 | 34.9 | 4.1 | 61.2 |
| 100 mg AlMgO/ (Half Conc) | 95.2 | 69.2 | 0.5 | 51.8 | 9.5 | 0.6 | 61.9 |

Example 5

Aldol Condensation of 2,5-Hexanedione at 80° C.

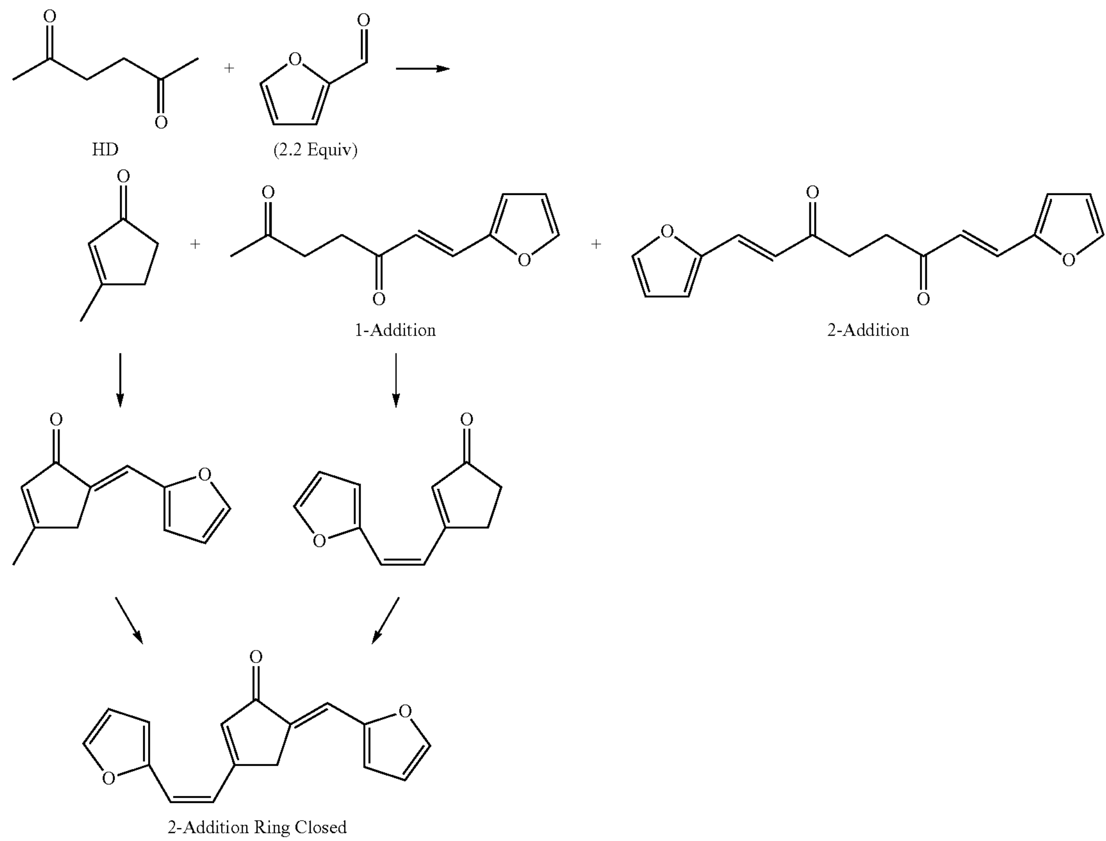

2-Addition Ring Closed

Toluene (Fisher), 2,5-hexanedione (Fluka), and dodecane (Aldrich) were used as received. Furfural (Aldrich) was freshly distilled prior to use. MgAlO was calcined as described in Example 1. "Mixture 1" of 1.639 g (126 mg (1.312 mmol)/reactor) furfural, 561.5 mg dodecane (43.2 mg/reactor), 884.5 mg 2,5-hexanedione (68.0 mg (0.597 mmol)/reactor) and 11.31 g toluene was prepared in a scintillation vial. "Mixture 2" of 1.878 g (144 mg (1.312 mmol)/reactor) 5-methylfurfural, 561.5 mg dodecane (43.2 mg/reactor), 884.5 mg 2,5-hexanedione (68.0 mg (0.597 mmol)/reactor) and 11.31 g toluene was prepared in a scintillation vial. "Mixture 3" of 224.6 mg dodecane (43.2 mg/reactor), 353.8 mg 2,5-hexanedione (68.0 mg (0.597 mmol)/reactor) and 4.524 (0.87 g/reactor) g toluene was prepared in a scintillation vial. A portion of each mixture, water, and the basic catalyst were added to a scintillation vial as set forth in Table 4 below.

TABLE 4

| Reactor | | Amt Water (g) | Base Amount (mg) | Reaction Time (hr) | Temp (° C.) |
|---|---|---|---|---|---|
| | Amt. Mix. 1 (g) | | | | |
| 1 | 1.108 g | 1.00 g | 10.0 MgAlO | 25 | 80 |
| 2 | 1.108 g | 1.00 g | 25.0 MgAlO | 25 | 80 |
| 3 | 1.108 g | 1.00 g | 50.0 MgAlO | 25 | 80 |
| 4 | 1.108 g | 1.00 g | 100.0 MgAlO | 25 | 80 |
| 5 | 1.108 g | 1.00 g | 150.0 MgAlO | 25 | 80 |
| 6 | 1.107 g + 0.870 g fresh Toluene | 1.00 g | 200.0 MgAlO | 25 | 80 |
| 7 | 1.108 g | 1.00 g | 12.5 μL of 2M NaOH | 25 | 80 |
| 8 | 1.108 g | 1.00 g | 25.0 μL of 2M NaOH | 25 | 80 |
| 9 | 1.108 g | 0.95 g | 50.0 μL of 2M NaOH | 25 | 80 |
| 10 | 1.108 g | 0.90 g | 100.0 μL of 2M NaOH | 25 | 80 |
| 11 | 1.107 g + 0.870 g fresh Toluene | — | 25.0 MgAlO | 25 | 80 |
| 12 | 1.107 g + 0.870 g fresh Toluene | — | 50.0 MgAlO | 25 | 80 |
| | Amt. Mix. 2 (g) | | | | |
| 13 | 1.126 g | 1.00 g | 10.0 MgAlO | 25 | 80 |
| 14 | 1.126 g | 1.00 g | 25.0 MgAlO | 25 | 80 |
| 15 | 1.126 g | 1.00 g | 50.0 MgAlO | 25 | 80 |

TABLE 4-continued

| Re-actor | | Amt Water (g) | Base Amount (mg) | Reaction Time (hr) | Temp (° C.) |
|---|---|---|---|---|---|
| 16 | 1.126 g | 1.00 g | 100.0 MgAlO | 25 | 80 |
| 17 | 1.126 g | 1.00 g | 150.0 MgAlO | 25 | 80 |
| 18 | 1.126 g | 1.00 g | 200.0 MgAlO | 25 | 80 |
| 19 | 1.126 g | 1.00 g | 12.5 μL of 2M NaOH | 25 | 80 |
| 20 | 1.126 g | 1.00 g | 25.0 μL of 2M NaOH | 25 | 80 |
| 21 | 1.126 g | 0.95 g | 50.0 μL of 2M NaOH | 25 | 80 |
| 22 | 1.126 g | 0.90 g | 100.0 μL of 2M NaOH | 25 | 80 |
| | Amt. Mix. 3 (g) | | | | |
| 23 | 0.981 g | 1.00 g | 25.0 MgAlO | 25 | 80 |
| 24 | 0.981 g | 1.00 g | 50.0 MgAlO | 25 | 80 |
| 25 | 0.981 g + 0.870 g fresh Toluene | — | 25.0 MgAlO | 25 | 80 |
| 26 | 0.981 g + 0.870 g fresh Toluene | — | 50.0 MgAlO | 25 | 80 |

Figure 2:
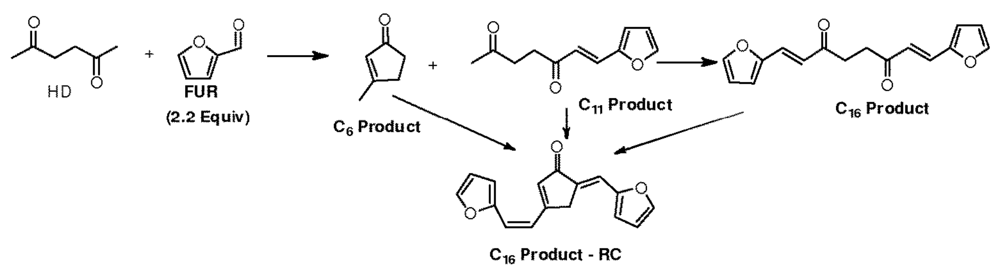
FIG. 2 depicts the data obtained for the cross-aldol condensation of 2,5-hexanedione and furfural at different basic catalyst loadings.
Figure 2:
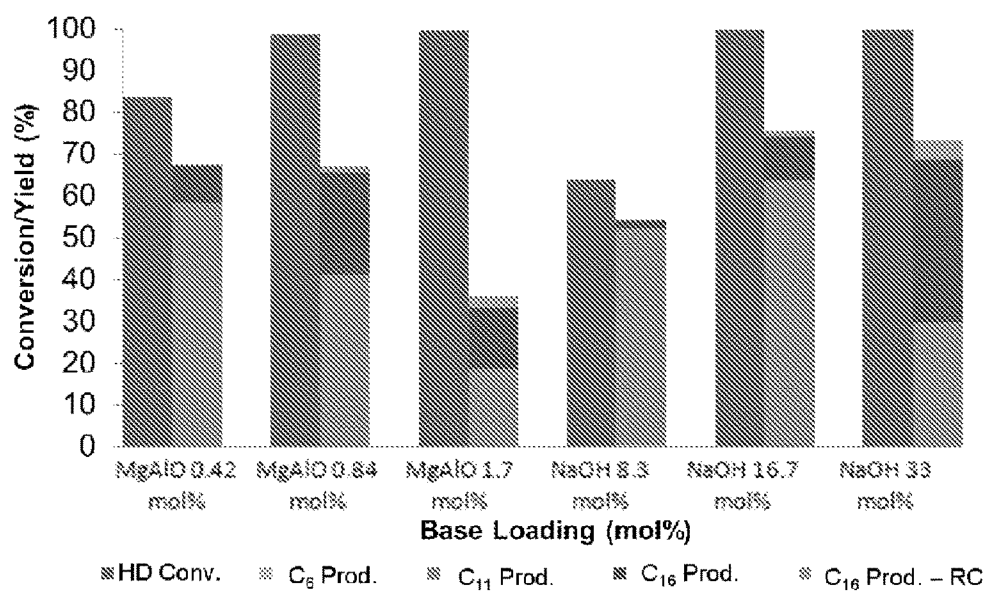
Figure 3:
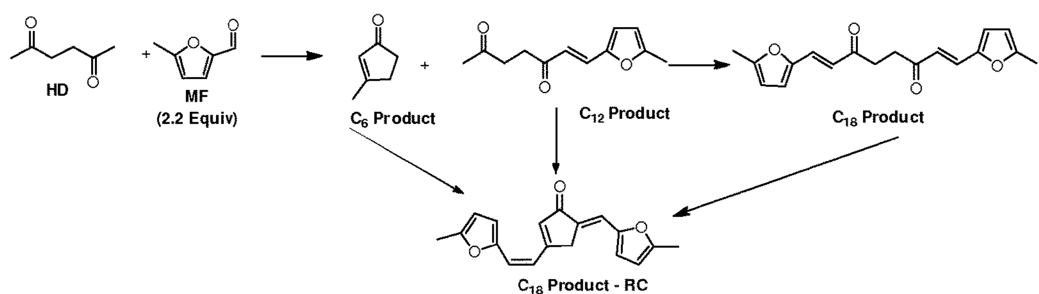
FIG. 3 depicts the data obtained for the cross-aldol condensation of 2,5-hexanedione and 5-methylfurfural at different basic catalyst loadings.
Figure 3:
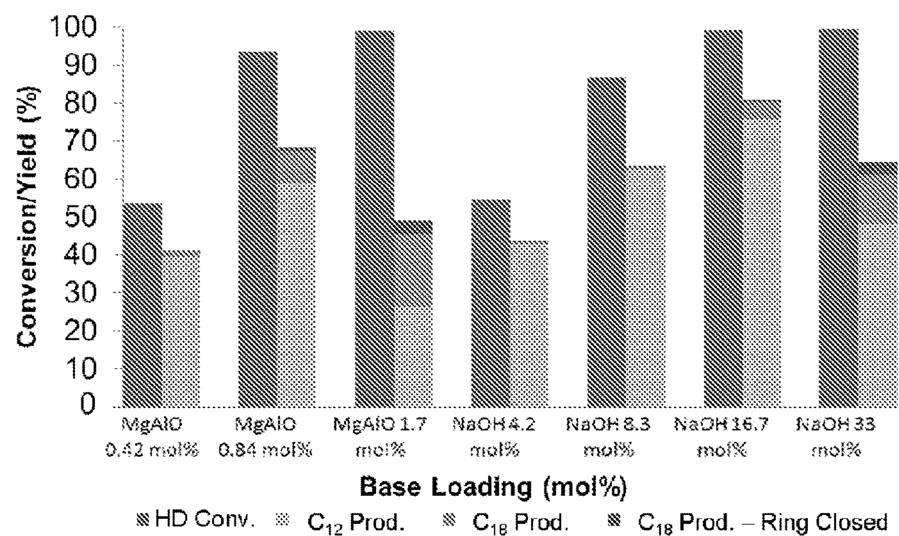

The reactors were placed on pre-heated stir plates and stirred at 800 RPM. For each reactor, all material was transferred to a 15 mL centrifuge tube. The transfer was completed with 2×2 mL ethanol washed. The 6 mL mixture was shaken and became one phase. The mixture was centrifuged at 4000 RPM. The organic layer was collected in a second 15 mL centrifuge tube. A sample from the organic layer was analyzed by GC. A comparison of the 25° C., 50° C., and 80° C. data is shown in FIG. 1. Results for furfural are summarized in FIG. 2. Results for 5-methylfurfural are summarized in FIG. 3.

Example 6

Aldol Condensation of 2,5-Hexanedione and 0-6 Equivalents of Furfural at 170° C.

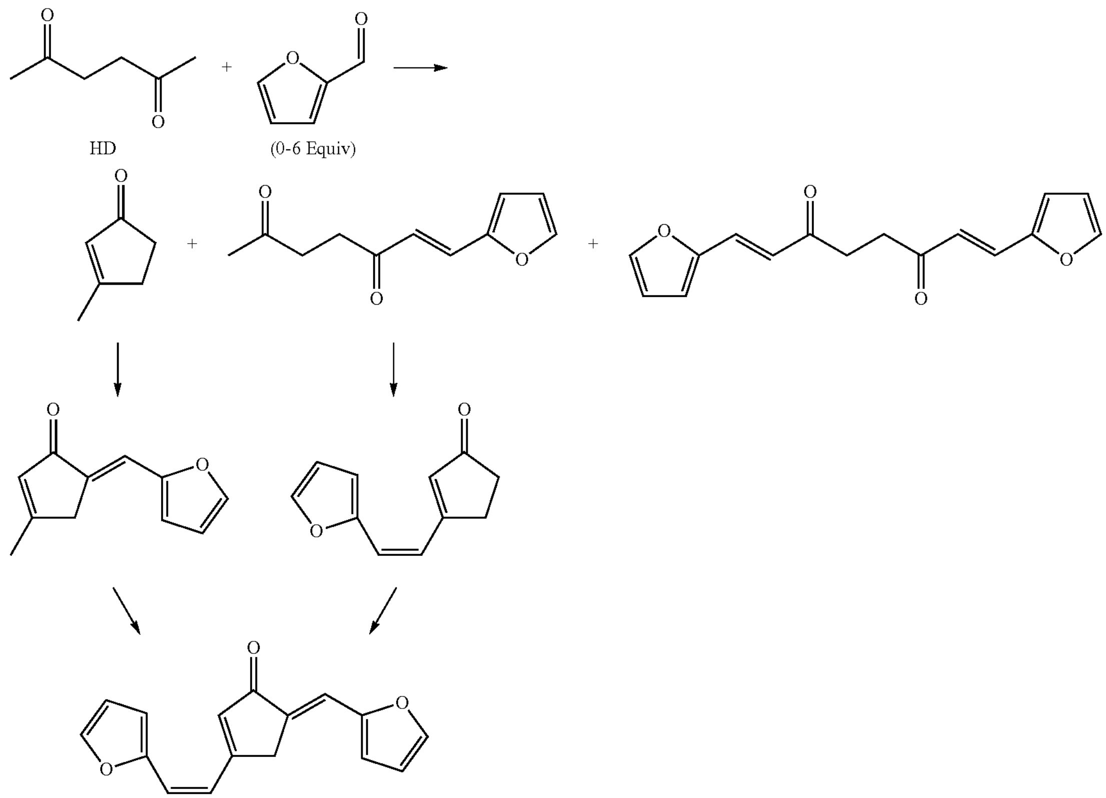

Toluene (Fisher), 2,5-hexanedione (Fluka), and dodecane (Aldrich) were used as received. Furfural (Aldrich) was freshly distilled prior to use. A mixture of 561.6 mg dodecane (86.4 mg/reactor), 884.7 mg 2,6-hexanedione (136.1 mg (1.19 mmol)/reactor), and 11.31 g (1.74 g/reactor) toluene was prepared in a small beaker. The quantities of the mixture and the MgAlO catalyst (calcined as described in Example 1) as set forth in Table 5 below were added to each Q-Tube (catalyst was added first).

TABLE 5

| Reactor | Amt. Mixture (g) | Amt Water (g) | Furfural Amt.(mg) (mol Equiv) | MgAlO Amount (mg) | Reaction Time (hr) | Temp (° C.) |
|---|---|---|---|---|---|---|
| 1 | 1.9625 | 2.00 g | 0 (0 equ.) | 200.0 | 4 | 170 |
| 2 | 1.9625 | 2.00 g | 57.1 (0.5) | 200.0 | 4 | 170 |
| 3 | 1.9625 | 2.00 g | 114.2 (1) | 200.0 | 4 | 170 |
| 4 | 1.9625 | 2.00 g | 228.5 (2) | 200.0 | 4 | 170 |
| 5 | 1.9625 | 2.00 g | 457.0 (4) | 200.0 | 4 | 170 |
| 6 | 1.9625 | 2.00 g | 685.4 (6) | 200.0 | 4 | 170 |

Figure 4:
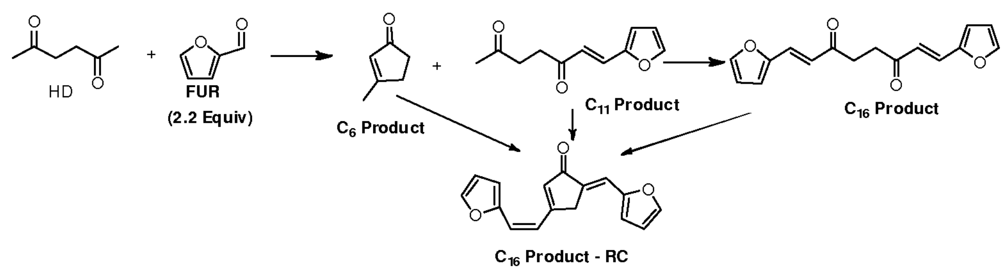
FIG. 4 depicts the data obtained for the cross-aldol condensation of 2,5-hexanedione and furfural at different furfural:2,5-hexanedione ratios.
Figure 4:
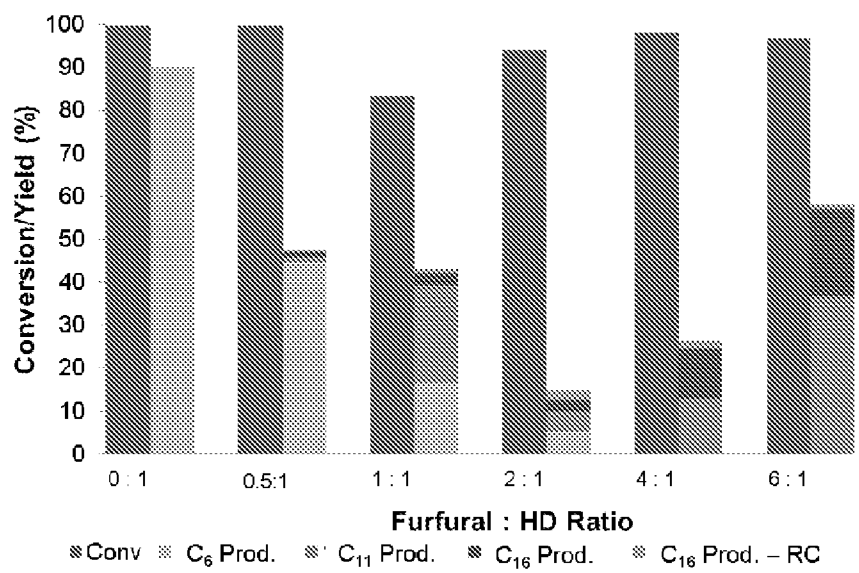

The reactors were placed on pre-heated stir plates and stirred at 800 RPM. For each reactor, all material was transferred to a 15 mL centrifuge tube and centrifuged at 4000 RPM. The organic layer was collected in a second 15 mL centrifuge tube. The aqueous phase was washed 3 more times with 4 mL of EtOAc and centrifuged. The organic fractions were combined and dried with $Na_2SO_4$. The results are summarized in FIG. 4.

Example 7

Crossed Aldol Condensation of 2,5-Hexanedione with Butanal

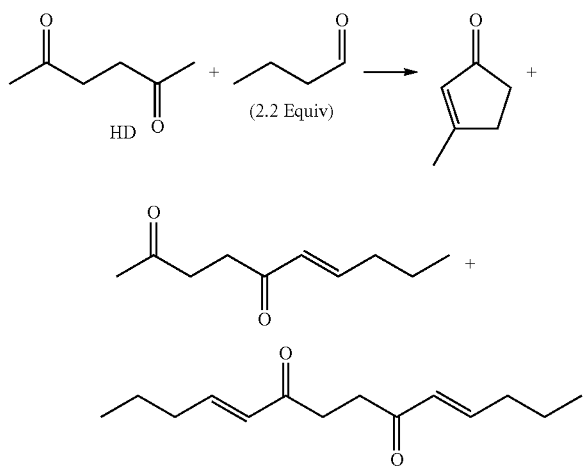

Butanol (Mallinckrodt Chemicals), $K_3PO_4$ (Acros), 2,5-hexanedione (Aldrich), and dodecane (Aldrich) was used as received. The reagents set forth in Table 6 below were added in glass headspace vials.

TABLE 6

| Reactor | Amt. Solvent (g) | Sec. Solvent (g) | DD (mg) | HD (mg) (2.385 mmol) | Butanal (mg) | $K_3PO_4$ (50 mol %) (mg) | Temp (° C.) |
|---|---|---|---|---|---|---|---|
| A | 3.48 g - Toluene | None | 172.7 | 272.2 | 343.9 | 253.1 | 100 |
| B | 3.48 g - Toluene | None | 172.7 | 272.2 | 687.9 | 253.1 | 100 |
| C | 3.24 g - Butanol | None | 172.7 | 272.2 | 343.9 | 253.1 | 100 |
| D | 3.24 g - Butanol | None | 172.7 | 272.2 | 687.9 | 253.1 | 100 |
| E | 4.00 g - Water | None | 172.7 | 272.2 | 343.9 | 253.1 | 100 |
| F | 4.00 g - Water | 3.24 (Butanol) | 172.7 | 272.2 | 343.9 | 253.1 | 100 |
| Init | 3.48 g - Toluene | None | 172.7 | 272.2 | 343.9 | 0 | 25 |

The vials were heated to 100° C. and stirred at 600 RPM for two hours. At the end of the reaction, the vials were cooled. The reactions were analyzed by GC. Cross-aldol products, butanal degradation products, and butanal self-aldolization products were observed.

Example 8

Self-Aldol Condensation of 2,5-Hexanedione to 3-Methylcyclopent-2-enone (MCP) Catalyst Study Toluene obtained from Fisher, 2,5-hexanedione obtained from Fluka, and dodecane obtained from Sigma Aldrich were used as received. The MgAlO, MgZrOx, and MgO catalysts were calcined at 700° C., 600° C., and 450° C., respectively. Basic $Al_2O_3$ (Fisher 60-325 mesh), $K_3PO_4$ (Tribasic, 97% pure, Anhydrous, Acros), and $TiO_2$ (anatase nanostructured) were used as received.

A mixture of 22.62 g toluene (4 mL/3.48 g per reactor), 561.6 mg dodecane (86.4 mg per reactor), and 884.7 mg 2,5-heaxanedione (1.19 mmol/136.1 mg per reactor) was prepared in a small beaker. 3.703 g of the mixture was added to seven individual reactor tubes in a high pressure glass reactor system for reaction up to 200 psi (Q-Tube system). 25 mg of catalyst was added to each reactor tube. The reactors were stirred at 800 RPM and heated at 180° C. for 0.75 or 2 hours. Upon cooling, all material was transferred from a reactor tube to a 15 mL centrifuge tube. The tube was centrifuged at 4000 RPM for 10 minutes. A sample of the separated organic layer was analyzed by GC. The results are summarized in Table 7 below.

TABLE 7

| Entry | Time (Hour) | Temp. (Deg C.) | Catalyst (40 mg) | Solvent | Conversion HD (%) | Yield MCP (%) | Sel. MCP (%) |
|---|---|---|---|---|---|---|---|
| 1 | 0.75 | 180 | $K_3PO_4$ | Toluene | 35 | 31 | 89 |
| 2 | 0.75 | 180 | Basic $Al_2O_3$ | Toluene | 94 | 78 | 84 |
| 3 | 0.75 | 180 | $TiO_2$ | Toluene | 74 | 53 | 71 |
| 4 | 0.75 | 180 | MgO | Toluene | 99 | 78 | 78 |
| 5 | 0.75 | 180 | MgZrO | Toluene | 89 | 82 | 93 |
| 6 | 0.75 | 180 | MgAlO | Toluene | 94 | 75 | 80 |
| 7 | 2 | 180 | MgAlO | Water/Toluene | 85.2 | 84.5 | 99 |
| 8 | 2 | 180 | MgAlO (50 mg) | Water/Toluene | 95.7 | 94.3 | 99 |

Example 9

Effect of Calcination Temperature on Hydrotalcite-Derived Materials on 2,5-Hexanedione Cyclization to 3-Methylcyclopent-2-enone (MCP)

25.00 g of synthetic hydrotalcite obtained from Aldrich ($CH_{16}Al_2Mg_6O_{19}.4H_2O$; Catalogue: 652288-1 kg) was measured out into a ceramic boat. The calcination furnace temperature was heated at 2° C./min (profile 4) under air to the final temperature. The furnace was held at the final temperature for 1 hour, then cooled to 250° C. and held at temperature. The hot hydrotalcite was removed from the furnace and covered until cool. The calcined hydrotalcite was massed and stored for later use. The final hydrotalcite masses are summarized in Table 8 below.

TABLE 8

| Calcination Temp (° C.) | Final MgAlO Mass (g) |
|---|---|
| 650 | 14.113 |
| 450 | 14.816 |
| 500 | 14.429 |
| 550 | 14.272 |
| 600 | 14.178 |
| 700 | 13.939 |

The cyclization reaction of 2,5-hexanedione was carried out as described in Example 8, above, at 180° C., 1.5 hr, 1.19 mmol 2,5-hexanedione, 4 mL toluene, and 40 mg MgAlO. Calcination in the range of 500-550° C. provided optimal catalyst activity (90-95% 2,5-hexanedione conversion) in the single-phase organic system. However, the cyclization reaction of 2,5-hexanedione was carried out in a biphasic system as described in Example 8, above, at 180° C., 1.5 hr, 1.19 mmol 2,5-hexanedione, 2 mL toluene, 2 mL water, and 20 mg MgAlO. Calcination at 700° C. for a 2-hour hold had the highest conversion at approximately 50%.

Example 10

Self-Aldol Condensation of 2,5-Hexanedione to 3-Methylcyclopent-2-enone (MCP) MgAlO and MgO in Toluene A mixture of 29.0 g toluene, 1.44 g dodecane, and 2.269 g 2,5-hexanedione was prepared in a small beaker. 3.925 g of the mixture was added to eight individual to reactor tubes in a Q-Tube system. 40 mg of catalyst (either MgAlO calcined at 450-700° C. or MgO calcined at 450° C.) was added to each reactor tube. The reactors were stirred at 800 RPM and heated at 180° C. for 2.0 hours. Upon cooling, all material was transferred from a reactor tube to a 15 mL centrifuge tube. The tube was centrifuged at 4000 RPM. The organic layer was collected in a second 15 mL centrifuge tube. The aqueous phase was washed three more times with 4 mL of EtOAc, centrifuged, and all the organic extracts were combined and dried with sodium sulfate. A sample of the separated organic layer was analyzed by GC. The results are summarized in Table 9 below.

TABLE 9

| Catalyst | HD Conv. (%) | MCP Yield (mol %) | Quant. Larger Prod Yield (mass %) |
|---|---|---|---|
| MgAlO - 450° C. | 83.0 | 70.8 | 8.5 |
| MgAlO - 500° C. | 91.8 | 75.2 | 11.2 |
| MgAlO - 550° C. | 92.0 | 75.0 | 11.0 |
| MgAlO - 600° C. | 86.7 | 70.8 | 10.4 |
| MgAlO - 650° C. | 83.7 | 69.6 | 9.5 |
| MgAlO - 700° C. | 84.7 | 69.3 | 9.7 |
| MgAlO - 700° C. (Batch 2) | 76.3 | 62.7 | 8.7 |
| MgO - 450° C. | 41.9 | 36.5 | 1.7 |

Example 11

Self-Aldol Condensation of 2,5-Hexanedione to 3-Methylcyclopent-2-enone (MCP) MgAlO and MgO in Toluene and Water A mixture of 14.5 g toluene, 0.720 g dodecane, and 1.135 g 2,5-hexanedione was prepared in a small beaker. 1.963 g of the mixture was added to eight individual to reactor tubes in a Q-Tube system. 20 mg of catalyst (either MgAlO calcined at 450-700° C. or MgO calcined at 450° C.) was added to each reactor tube. 2.000 g of water was added to each reactor tube. The reactors were stirred at 800 RPM and heated at 180° C. for 1.5 hours. Upon cooling, all material was transferred from a reactor tube to a 15 mL centrifuge tube. The tube was centrifuged at 4000 RPM. The organic layer was collected in a second 15 mL centrifuge tube. The aqueous phase was washed three more times with 4 mL of EtOAc, centrifuged, and all the organic extracts were combined and dried with sodium sulfate. A sample of the separated organic layer was analyzed by GC. The results are summarized in Table 10 below.

TABLE 10

| Catalyst | HD Conv. (%) | MCP Yield (mol %) | Quant. Larger Prod Yield (mass %) |
|---|---|---|---|
| MgAlO - 450° C. | 17.6 | 17.1 | 0.1 |
| MgAlO - 500° C. | 16.1 | 15.7 | 0.1 |

TABLE 10-continued

| Catalyst | HD Conv. (%) | MCP Yield (mol %) | Quant. Larger Prod Yield (mass %) |
|---|---|---|---|
| MgAlO - 550° C. | 22.0 | 21.4 | 0.2 |
| MgAlO - 600° C. | 24.7 | 24.5 | 0.2 |
| MgAlO - 650° C. | 24.8 | 24.7 | 0.1 |
| MgAlO - 700° C. | 40.5 | 40.3 | 0.5 |
| MgAlO - 700° C. (Batch 2) | 49.0 | 48.1 | 0.4 |
| MgO - 450° C. | 2.8 | 2.8 | 0.1 |

Example 12

Hydrogenation of 3-Methylcyclopent-2-enone (MCP)

3-methylcyclopent-2-enone (MCP, Aldrich), octanol (Fluka Analytical), dichloromethane (Sigma Aldrich), and dodecane (Sigma Aldrich) were used as received. Pd/C (Acros), Pd/$Al_2O_3$ (Aldrich), Pt/C (Acros), Pt/$Al_2O_3$ (Aldrich), Ru/C (Acros), Ru/$Al_2O_3$ (Aldrich), Rh/C (Aldrich), and Rh/$Al_2O_3$ (Aldrich) were dried for 2 hours at high vacuum at 60° C. prior to use. A HEL ChemSCAN reactor was used for the reaction. A HEL reactor is a multiple autoclave system. Each of the 8 hastelloy autoclaves on the system has a 15 mL capacity and is magnetically stirred. Each reactor can also have pressure and temperature varied independently from each other. In each HEL reactor, 100 mg MCP, 100 mg dodecane, 1.8 g octanol, and the catalyst were added as set forth in Table 11 below.

TABLE 11

| Reactor | Temp (Deg C.) | Pressure (PSI) | Mixture (g) | Catalyst (mg) |
|---|---|---|---|---|
| 1 | 70 | 150 | 2 | 11.1 - Pd/C |
| 2 | 70 | 150 | 2 | 22.1 - Pd/$Al_2O_3$ |
| 3 | 70 | 150 | 2 | 40.6 - Pt/C |
| 4 | 70 | 150 | 2 | 40.6 - Pt/$Al_2O_3$ |
| 5 | 70 | 150 | 2 | 21.0 - Ru/C |
| 6 | 70 | 150 | 2 | 21.0 - Ru/$Al_2O_3$ |
| 7 | 70 | 150 | 2 | 21.4 - Rh/C |
| 8 | 70 | 150 | 2 | 21.4 - Rh/$Al_2O_3$ |

The reactor was started with 2 purges of $N_2$ and 2 purges of $H_2$. Stirring was started at 500 RPM at the beginning of the reaction to prevent the catalyst from settling. The temperature was set to 70° C., pressure to 150 psi, and stirring to 500 RPM. After 5 hours, the reactors were cooled and vented. The combined solid and liquid were transferred into a 15 mL centrifuge tube and centrifuged for 20 min at 4000 RPM. A sample from the organic layer was analyzed by GC. The results are summarized in Table 12 below.

TABLE 12

| Catalyst | MCP Conv. (%) | Ketone Yield (mol %) | Alcohol Yield (mol %) | Alkane Yield (mol %) |
|---|---|---|---|---|
| Pd/C | 100.0 | 98.8 | 2.9 | 0.0 |
| Pd/$Al_2O_3$ | 100.0 | 91.6 | 9.2 | 0.0 |
| Pt/C | 100.0 | 81.5 | 7.2 | 7.8 |
| Pt/$Al_2O_3$ | 100.0 | 0.2 | 76.4 | 4.8 |
| Ru/C | 100.0 | 0.5 | 81.9 | 0.1 |
| Ru/$Al_2O_3$ | 100.0 | 41.0 | 46.8 | 1.4 |
| Rh/C | 100.0 | 22.6 | 39.2 | 3.1 |
| Rh/$Al_2O_3$ | 100 | 71.9 | 24.0 | 0.0 |

Example 13

Hydrogenolysis of MCP 3-methylcyclopent-2-enone (MCP, Aldrich), octanol (Fluka Analytical), dichloromethane (Sigma Aldrich), and dodecane (Sigma Aldrich) were used as received. Pt/C (Acros), Ru/C (Acros), and Amberlyst 70 (Dow) were dried for 2 hours at high vacuum at 60° C. prior to use. In each HEL reactor, the components set forth in Table 13 below were added.

TABLE 13

| Reactor | Temp (Deg C.) | Solvent (g) | Pressure (PSI) | Metal Catalyst (mg) | Acid Catalyst A-70 (mg) |
|---|---|---|---|---|---|
| 1 | 170 | 1.8 g Toluene | 450 | 40.6 - Pt/C | 8.2 mg - A-70 |
| 2 | 170 | 1.8 g Octanol | 450 | 40.6 - Pt/C | 8.2 mg - A-70 |
| 3 | 170 | 1.8 g Toluene | 450 | 40.6 - Pt/C | — |
| 4 | 170 | 1.8 g Octanol | 450 | 40.6 - Pt/C | — |
| 5 | 170 | 1.8 Water/1.292 Octane | 450 | 40.6 - Pt/C | 8.2 mg - A-70 |
| 6 | 170 | 1.8 Water/1.566 Toluene | 450 | 40.6 - Pt/C | 8.2 mg - A-70 |
| 7 | 170 | 1.8 Water/1.483 Octanol | 450 | 40.6 - Pt/C | 8.2 mg - A-70 |
| 8 | 170 | 0.9 Water/0.783 Toluene | 450 | 20.3 - Pt/C | 4.1 mg - A-70 |

The reactor was started with 2 purges of $N_2$ and 2 purges of $H_2$. Stirring was started at 500 RPM at the beginning of the reaction to prevent the catalyst from settling. The temperature was set to 170° C., pressure to 450 psi, and stirring to 500 RPM. After 6 hours, the reactors were cooled and vented. The combined solid and liquid were transferred into a 15 mL centrifuge tube and centrifuged for 5 min at 4000 RPM. A sample from the organic layer was analyzed by GC. The results are summarized in Table 14 below.

TABLE 14

| Catalyst System | Solvent System | MCP Conv. (%) | Ketone Yield (mol %) | Alcohol Yield (mol %) | Alkane Yield (mol %) |
|---|---|---|---|---|---|
| Pt/C | Toluene | 100.0 | 3.5 | 75.6 | 11.6 |
| Pt/C + A-70 | Toluene | 100.0 | 0.1 | 0.0 | 81.3 |
| Pt/C | Octanol | 100.0 | 57.2 | 19.9 | 12.1 |
| Pt/C + A-70 | Octanol | 99.9 | 7.5 | 3.9 | 47.9 |
| Pt/C + A-70 | Water/Octane | 100.0 | 2.5 | 9.2 | 55.9 |
| Pt/C + A-70 | Water/Toluene | 100.0 | 1.2 | 28.2 | 45.5 |
| Ru/C + A-70 | Water/Octanol | 100.0 | 60.5 | 11.7 | 16.7 |
| Pt/C + A-70 | Water/Toluene | 100.0 | 1.3 | 33.7 | 38.2 |

Example 14

Guerbet Reaction of 1-Tetradecanol to $C_{28}$-Alcohol

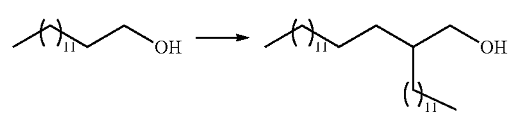

The Guerbet reaction was carried out in a 4560 mini Parr reactor. In a 50 mL reactor, 1-tetradecanol (10 g, 47 mmol), 5% palladium on carbon (containing 50% of water, 0.06 mg, 0.14 mmol), potassium phosphate tribasic (3.5 g, 16.5 mmol), toluene (15 mL) were added. The reaction vessel was sealed and the mixture was stirred at 220° C. for 6 days. The GC analysis of the crude mixture revealed that the mixture mainly consisted of C28-alcohol and unreacted starting material in 1:1 ratio. The reaction mixture was filtered over celite and was washed with EtOH. The solvent was evaporated and a new batch of 5% palladium on carbon (containing 50% of water, 0.06 mg, 0.14 mmol), potassium phosphate tribasic (3.5 g, 16.5 mmol), toluene (15 mL) were added. The reaction mixture was further stirred for 6 days. The mixture was filtered over celite to provide C28-OH in 75% overall yield.

Example 15

2-Butanone and 1,6-Hexanediol to $C_{10}$ Ketone

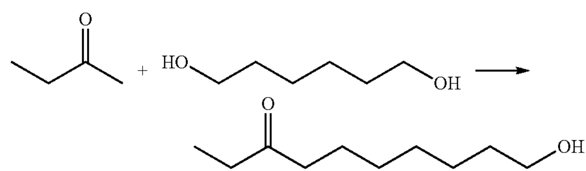

In a 12 mL Q-Tube (pressure tube) 5% palladium on carbon (containing 50% of water, 5.5 mg, 0.0013 mmol), potassium phosphate tribasic (34 mg, 0.16 mmol) and magnetic stir bar were placed. To the tube, 1.0 mL of toluene was added followed by 2-butanone (360.5 mg, 5.0 mmol), 1,6-hexanediol (118.2 mg, 1.0 mmol) and dodecane (internal standard) were added. The Q-tube was sealed and the reaction mixture was stirred at 145° C. in the pre-heated metal block for 20 h at the same temperature after which the tube was cooled to room temperature. The sample diluted with THF and GC analysis of the reaction mixture yielded the amount of product (57% yield).

The reaction described above in this Example was repeated using other diols, including 1,3-propanediol, 1,4-butanediol, and 1,5-pentanediol. No keto-alcohol product was observed from such reactions using palladium on carbon as the catalyst, potassium phosphate tribasic as the base, and toluene as the solvent.

Example 16

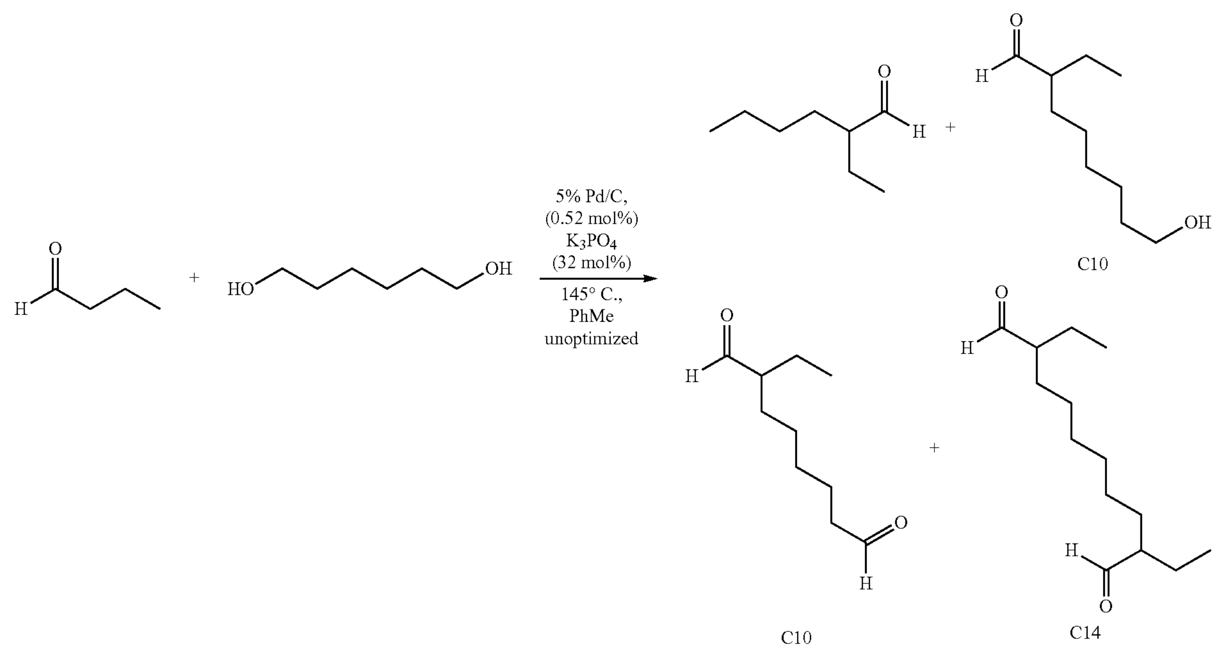

In a 12 mL Q-Tube (pressure tube) 5% palladium on carbon (containing 50% of water, 11 mg, 0.0026 mmol), potassium phosphate tribasic (68 mg, 0.32 mmol) and magnetic stir bar were placed. To the tube, butyraldehyde (72.1 mg, 1.0 mmol), 1,6-hexanediol (177 mg, 1.5 mmol), toluene (1 mL) and dodecane (internal standard) were added. The tube was sealed and the reaction mixture was stirred for 20 hours at 145° C. in the pre-heated metal block. The reaction mixture was cooled to room temperature and the sample diluted with THF. GC analysis of the reaction mixture showed the formation of higher molecular weight compounds whose structures were tentatively assigned.

Example 17

Acetone and 2-Ethylhexanol to $C_{11}$ Ketone

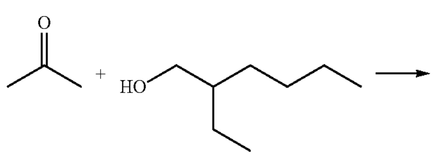

-continued

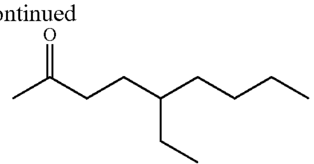

In a 12 mL Q-Tube (pressure tube) 5% palladium on carbon (containing 50% of water, 2.0 mg), potassium phosphate tribasic (64 mg) and magnetic stir bar were placed. To the tube, 1.0 mL of toluene was added followed by 2-ethylhexanol (1.0 mmol), acetone (2.2 mmol) and dodecane (internal standard) were added. The Q-tube was sealed and the reaction mixture was stirred at 200° C. in the pre-heated metal block for 20 h at the same temperature after which the tube was cooled to room temperature. The sample diluted with THF and GC analysis of the reaction mixture yielded the amount of $C_{11}$ product (25% yield) and some $C_{19}$ product (8% yield).

Example 18

2-Butanone and 1,6-Hexanediol to $C_{10}$ Ketone

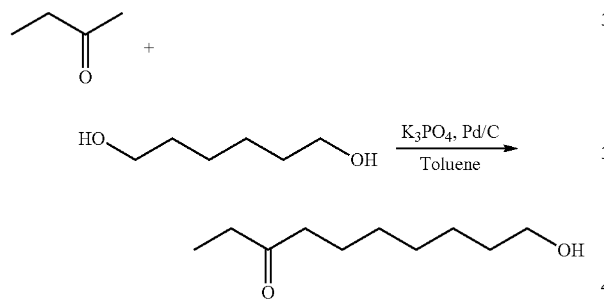

The reaction depicted above was performed according to the procedure described in Example 15 above. The amounts of 2-butanone and hexanediol, the type and amount of metal and base, the type of solvent, and the temperature of the reaction is specified in Table 15 below. Table 15 below also summarizes the yield of the $C_{10}$ ketone produced.

TABLE 15

| 2-Butanone | Hexanediol | Metal | Base | Solvent | Temp (° C.) | Yield |
|---|---|---|---|---|---|---|
| 1 mmol | 1.2 mmol | Pd/C, 5.5 mg | $K_3PO_4$, 68 mg | Toluene | 145 | 20% |
| 2.2 mmol | 1 mmol | Pd/C, 5.5 mg | $K_3PO_4$, 68 mg | Toluene | 145 | 47% |
| 2.2 mmol | 1 mmol | Pd/C, 5.5 mg | $K_3PO_4$, 136 mg | Toluene | 145 | 14% |
| 2.2 mmol | 1 mmol | Pd/C, 5.5 mg | $K_3PO_4$, 68 mg | Toluene | 120 | 21% |
| 2.2 mmol | 1 mmol | Pd/C, 5.5 mg | $K_3PO_4$, 34 mg | Toluene | 120 | 24% |
| 2.2 mmol | 1 mmol | Pd/C, 11 mg | $K_3PO_4$, 68 mg | Toluene | 145 | 48% |
| 4.4 mmol | 1 mmol | Pd/C, 11 mg | $K_3PO_4$, 68 mg | Toluene | 145 | 38% |
| 5 mmol | 1 mmol | Pd/C, 5.5 mg | $K_3PO_4$, 21 mg | Toluene | 145 | 55% |
| 5 mmol | 1 mmol | Pd/C, 5.5 mg | $K_3PO_4$, 34 mg | Toluene | 145 | 57% |
| 5 mmol | 1 mmol | Pd/C, 5.5 mg | $K_3PO_4$, 42 mg | Toluene | 145 | 52% |
| 5 mmol | 1 mmol | Pd/C, 5.5 mg | $K_3PO_4$, 68 mg | Toluene | 145 | 40% |
| 2.2 mmol | 1 mmol | KOH, 18 mg | $K_3PO_4$, 68 mg | Toluene | 145 | NR |
| 2.2 mmol | 1 mmol | KOH, 18 mg | $K_3PO_4$, 68 mg | Dioxane | 145 | NR |
| 5 mmol | 1 mmol | Pd/C, 5.5 mg | $K_3PO_4$, 34 mg | Dioxane | 145 | 34% |

NR = trace amounts of products observed

Enumerated Items

The present disclosure includes the following items:

1. A method of producing one or more ketones comprising contacting a compound of formula (I) with basic catalyst and one or more alcohols or aldehydes of formula (II):

(I)

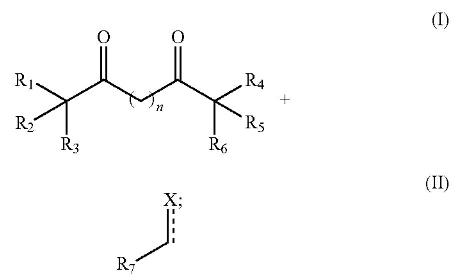

(II)

wherein:

each $R_1$, $R_2$, $R_3$, $R_4$, $R_5$, and $R_6$ is independently selected from the group consisting of hydrogen, $C_1$-$C_{20}$ alkyl, $C_6$-$C_{22}$ aryl, $C_2$-$C_{20}$ alkenyl, and $C_2$-$C_{20}$ alkynyl;

$R_7$ is selected from the group consisting of $C_1$-$C_{20}$ alkyl, $C_6$-$C_{20}$ aryl, $C_2$-$C_{20}$ alkenyl, $C_2$-$C_{20}$ alkynyl, and $C_4$-$C_{21}$ heteroaryl;

X is OH or 0;

at least two of $R_1$, $R_2$, and $R_3$ is hydrogen or at least two of $R_4$, $R_5$, and $R_6$ is hydrogen; and n is an integer greater than or equal to 0, and optionally n is 1-10;

to produce the one or more ketones.

2. The method of item 1, wherein the compound of formula (I) is:

(I)

3. The method of either item 1 or item 2, wherein the compound of formula (I) is:

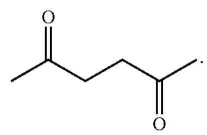

4. The method of any one of items 1 to 3, wherein the compound of formula (II) is:

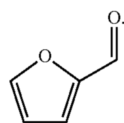

5. The method of any one of items 1 to 4, wherein $R_7$ is $C_1$-$C_{10}$ alkyl.

6. The method of any one of items 1 to 5, wherein $R_7$ is $C_4$ alkyl.

7. The method of any one of items 1 to 4, wherein $R_7$ is $C_4$-$C_{21}$ heteroaryl.

8. The method of any one of items 1 to 4 or 7, wherein $R_7$ is furanyl.

9. The method of any one of items 1 to 4 or 7 to 8, wherein $R_7$ is selected from the group consisting of furfural, 5-methylfurfural, and 5-hydroxymethylfurfural.

10. The method of any one of items 1 to 4 or 7 to 9, wherein the compound of formula (II)

O.

11. The method of any one of items 1 to 10, wherein the one or more ketones are selected from the group consisting of:

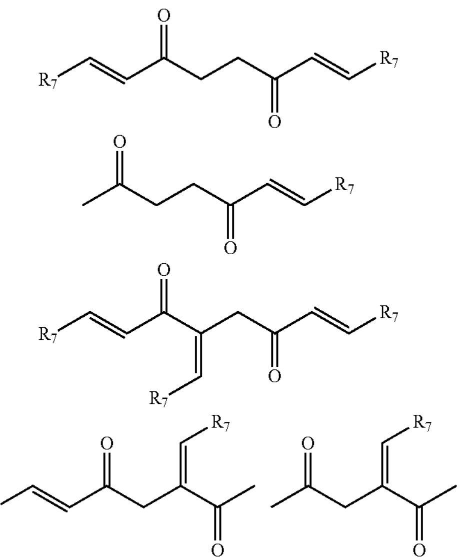

-continued

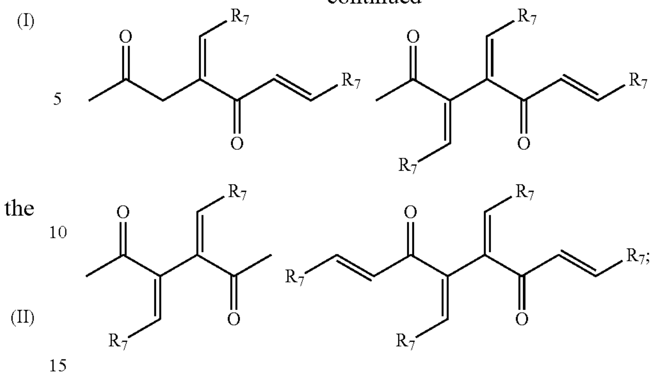

and mixtures thereof.

12. The method of any one of items 1 to 11, wherein the compound of formula (I) cyclizes to form one or more cyclic ketones.

13. The method of any one of items 1 to 12, wherein the one or more ketones cyclize to form one or more cyclic ketones.

14. The method of any one of items 1 to 13, wherein the one or more cyclic ketones react with the one or more alcohols or aldehydes of formula (II) to produce the one or more ketones.

15. The method of any one of items 1 to 14, wherein the one or more ketones are selected from the group consisting of:

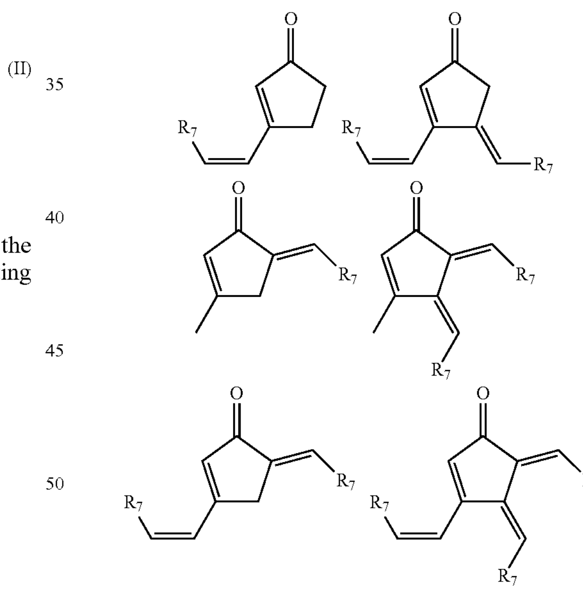

and mixtures thereof.

16. The method of any one of items 1 to 15, further comprising converting biomass to the compound of formula (I).

17. The method of any one of items 1 to 16, further comprising hydrolyzing a furan to produce the compound of formula (I).

18. The method of item 17, wherein the furan is dimethylfuran.

19. The method of item 18, further comprising hydrogenating 5-hydroxymethylfurfural to produce the dimethylfuran.

20. The method of any one of items 1 to 19, wherein the basic catalyst is an inorganic base.

21. The method of item 20, wherein the inorganic base is an alkali metal hydroxide or an alkaline earth metal hydroxide.

22. The method item 20, wherein the inorganic base is $K_3PO_4$.

23. The method of any one of items 1 to 19, wherein the basic catalyst is an organic base.

24. The method of any one of items 1 to 19, wherein the basic catalyst is a heterogeneous catalyst.

25. The method of item 24, wherein the heterogeneous catalyst comprises one or more metals selected from the group consisting of Mg, Al, Zr, Ti, Ce, B, and Y, and any mixture thereof.

26. The method of any one of items 1 to 19 and 24 to 25 wherein the basic catalyst is a mixed metal oxide.

27. The method of item 26, wherein the mixed metal oxide comprises MgZrO or MgAlO.

28. The method of either item 26 or item 27, wherein the mixed metal oxide comprises MgAlO.

29. The method of any one of items 1 to 28, wherein the contacting the compound of formula (I) with the basic catalyst occurs in a solvent, and wherein the solvent is an aqueous, organic, or biphasic aqueous and organic solvent.

30. The method of item 29, wherein the organic solvent is selected from the group consisting of toluene, trimethylacetonitrile, dimethylformamide, propyl-acetate, dioxane, butanol, hexanol, octanol, and any mixture thereof.

31. The method of either item 29 or item 30, wherein the organic solvent is toluene.

32. The method of any one of items 1 to 31, wherein at least 70% of the one or more ketones are branched ketones.

33. The method of any one of items 1 to 32, further comprising hydrogenating the one or more ketones to one or more alkanes.

34. The method of item 33, wherein the one or more alkanes are selected from the group consisting of:

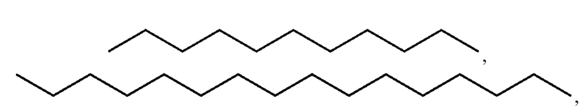

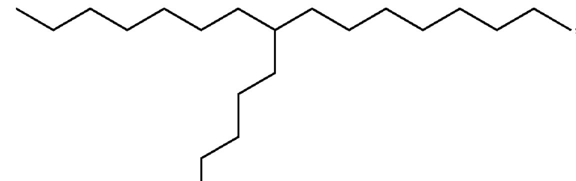

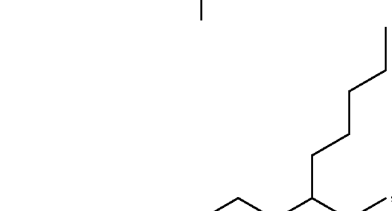

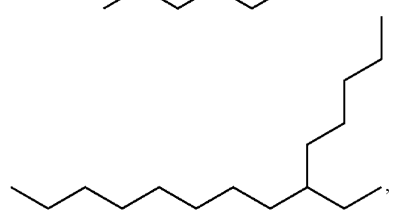

-continued

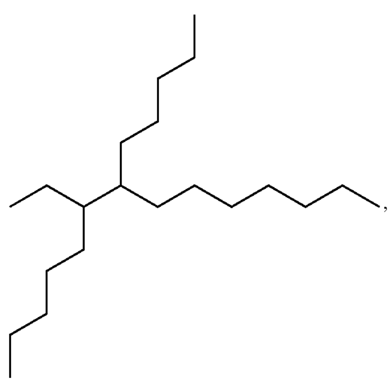

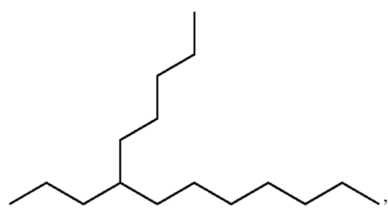

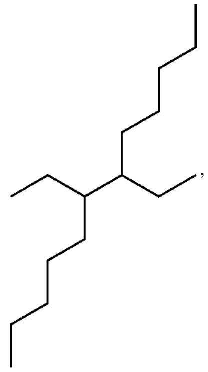

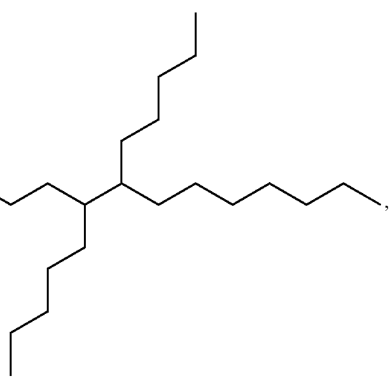

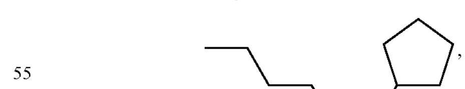

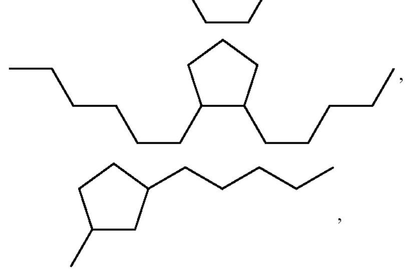

-continued

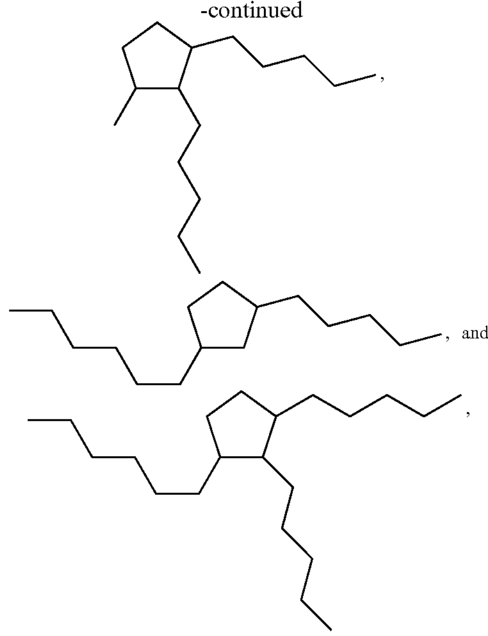

and mixtures thereof.

35. The method of item 33 or 34, wherein at least 70% of the one or more alkanes are $C_{11+}$ alkanes.

36. The method of any one of items 33 to 35, wherein at least 70% of the one or more alkanes are $C_{16+}$ alkanes.

37. The method of any one of items 33 to 36, wherein at least 70% of the one or more alkanes are $C_{21+}$ alkanes.

38. The method of any one of items 33 to 37, wherein at least 70% of the one or more alkanes are $C_{26+}$ alkanes.

39. The method of any one of items 1 to 32, further comprising hydrogenating the one or more ketones to produce an alcohol.

40. The method of item 39, further comprising reacting the alcohol with one or more alcohols to produce one or more branched alcohols.

41. The method of item 40, further comprising hydrogenating the one or more branched alcohols to produce one or more alkanes.

42. The method of item 41, wherein at least 70% of the one or more alkanes are $C_{11+}$ alkanes.

43. The method of item 41 or 42, wherein at least 70% of the one or more alkanes are $C_{16+}$ alkanes.

44. The method of any one of items 41 to 43, wherein at least 70% of the one or more alkanes are $C_{21+}$ alkanes.

45. The method of any one of items 41 to 44, wherein at least 70% of the one or more alkanes are $C_{26+}$ alkanes.

46. The method of any one of items 40 to 45, wherein the one or more alcohols comprises 1,6-hexanediol.

47. A method of producing one or more $C_{24}$-$C_{36}$ alkanes, comprising:

(a) contacting an aldehyde and one or more alcohols with a metal catalyst and optionally a base to produce one or more higher aldehydes;

(b) hydrogenating the one or more higher aldehydes to one or more higher alcohols; and (c) converting the one or more higher alcohols to the one or more $C_{24}$-$C_{36}$ alkanes.

48. The method of claim 47, wherein the one or more alcohols is one alcohol.

49. The method of claim 47, wherein the one or more alcohols are two alcohols.

50. The method of item 47, wherein the one or more aldehydes is a compound of formula (V) and the one or more alcohols is a compound of formula (IV):

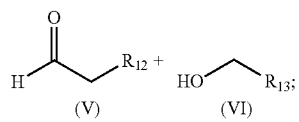

wherein each $R_{12}$ and $R_{13}$ is independently selected from the group consisting of $C_1$-$C_{10}$ alkyl, $C_6$-$C_{20}$ aryl, $C_2$-$C_{10}$ alkenyl, $C_2$-$C_{10}$ alkynyl, and $C_4$-$C_{21}$ heteroaryl.

51. The method of item 50, wherein the one or more higher aldehydes is a compound of formula (E):

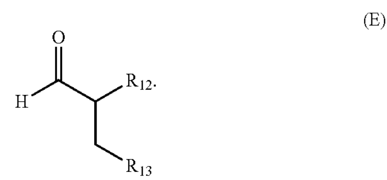

52. The method of any one of items 47 to 51, wherein the converting the one or more higher alcohols to one or more $C_{24}$-$C_{36}$ alkanes comprises dehydrating the one or more higher alcohols to one or more alkenes and oligomerizing the one or more alkenes to produce the one or more $C_{24}$-$C_{36}$ alkanes.

53. The method of any one of items 47 to 51, wherein the converting the one or more higher alcohols to one or more $C_{24}$-$C_{36}$ alkanes comprises hydrogenating the one or more higher alcohols to produce the one or more $C_{24}$-$C_{36}$ alkanes.

54. The method of any one of items 47 to 51, wherein the converting the one or more higher alcohols to one or more $C_{24}$-$C_{36}$ alkanes comprises (a) reacting the one or more higher alcohols with one or more alcohols, a metal catalyst, and optionally a base to produce one or more $C_{24}$-$C_{36}$ alcohols; and (b) hydrogenating the one or more $C_{24}$-$C_{36}$ alcohols to produce the one or more $C_{24}$-$C_{36}$ alkanes.

55. The method of any one of items 47 to 54, wherein at least one of the one or more alcohols is 1,6-hexanediol.

56. The method of any one of items 47 to 55, wherein the metal catalyst is Pd/C.

57. The method of any one of items 47 to 56, wherein the base is $K_3PO_4$.

58. The method of any one of items 47 to 57, wherein the aldehyde is acetaldehyde.

59. The method of any one of items 47 to 57, wherein the aldehyde is butyraldehyde.

60. A method of producing a cyclic alkane, cyclic alcohol, or mixtures thereof, comprising:

(a) contacting a diketone with basic catalyst to produce a cyclic ketone; and (b) hydrogenating the cyclic ketone to produce the cyclic alkane, cyclic alcohol, or mixtures thereof.

61. The method of item 60, wherein the diketone is a compound of formula I:

(I)

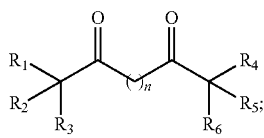

wherein:

each $R_1$, $R_2$, $R_3$, $R_4$, $R_5$, and $R_6$ is independently selected from the group consisting of hydrogen, $C_1$-$C_{10}$ alkyl, $C_6$-$C_{22}$ aryl, $C_2$-$C_{10}$ alkenyl, and $C_2$-$C_{10}$ alkynyl;

at least two of $R_1$, $R_2$, and $R_3$ is hydrogen or at least two of $R_4$, $R_5$, and $R_6$ is hydrogen; and n is 1-10.

62. The method of item 61, wherein the compound of formula I is:

(I)

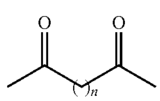

63. The method of either item 61 or item 62, wherein n=2.

64. The method of any one of items 60 to 63, wherein the cyclic alcohol is a compound of formula (Ia) or (Ib):

(Ia)

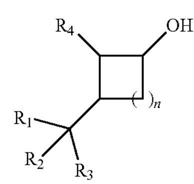

(Ib)

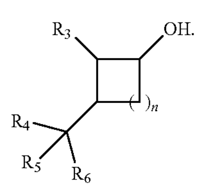

65. The method of any one of items 60 to 64, wherein the cyclic alkane is a compound of formula (Ic) or (Id):

(Ic)

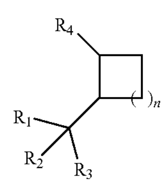

(Id)

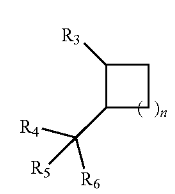

66. The method of any one of items 61 to 65, wherein the compound of formula (I) is:

(I)

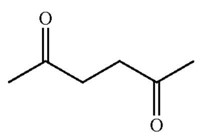

67. The method of any one of items 60 to 66, wherein the cyclic ketone is:

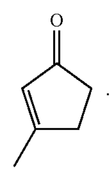

68. The method of any one of items 60 to 67, wherein the cyclic alcohol is:

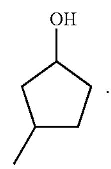

69. The method of any one of items 60 to 68, wherein the cyclic alkane is:

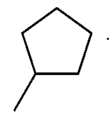

70. The method of any one of items 60 to 69, further comprising converting biomass to the diketone.

71. The method of any one of items 60 to 70, further comprising hydrolyzing a furan to produce the diketone.

72. The method of item 71, wherein the furan is dimethylfuran.

73. The method of item 72, further comprising hydrogenating 5-hydroxymethylfurfural to produce the dimethylfuran.

74. The method of any one of items 60 to 73, wherein the basic catalyst is an inorganic base.

75. The method of item 74, wherein the inorganic base is an alkali metal hydroxide or an alkaline earth metal hydroxide.

76. The method item 74, wherein the inorganic base is $K_3PO_4$.

77. The method of any one of items 60 to 73, wherein the basic catalyst is an organic base.

78. The method of any one of items 60 to 73, wherein the basic catalyst is a heterogeneous catalyst.

79. The method of item 78, wherein the heterogeneous catalyst comprises one or more metals selected from the group consisting of Mg, Al, Zr, Ti, Ce, B, and Y, and any mixture thereof.

80. The method of any one of items 60 to 73 or 78 to 79, wherein the basic catalyst is a mixed metal oxide.

81. The method of item 80, wherein the mixed metal oxide comprises MgZrO or MgAlO.

82. The method of either item 80 or item 81, wherein the mixed metal oxide comprises MgAlO.

83. The method of any one of items 60 to 82, wherein the contacting the diketone and the basic catalyst occurs in a solvent, and wherein the solvent is an aqueous, organic, or biphasic aqueous and organic solvent.

84. The method of item 83, wherein the organic solvent is selected from the group consisting of toluene, trimethylacetonitrile, dimethylformamide, propyl-acetate, dioxane, butanol, hexanol, octanol, and any mixture thereof.

85. The method of either item 83 or item 84, wherein the organic solvent is toluene.

86. The method of any one of items 60 to 85, wherein the conversion of the diketone to the cyclic ketone is at least 95%.

87. The method of any one of items 60 to 86, wherein the conversion of the diketone to the cyclic ketone is at least 99%.

88. The method of any one of items 60 to 87, wherein the cyclic ketone is formed from the diketone with at least 95% selectivity.

89. The method of any one of items 60 to 88, wherein the cyclic ketone is formed from diketone with at least 99% selectivity.

90. The method of any one of items 33 to 89, wherein the hydrogenating is carried out with a hydrogenation catalyst comprising one or more metals selected from the group consisting of Cu, Ni, Pt, Pd, Rh, Ru, and Ir.

91. The method of item 90, wherein the hydrogenation catalyst is selected from the group consisting of Pd/C, $Pd/Al_2O_3$, Pt/C, $Pt/Al_2O_3$, Ru/C, $Ru/Al_2O_3$, Rh/C, $Rh/Al_2O_3$, and mixtures thereof.

92. The method of item 91, wherein the hydrogenation catalyst is Pd/C or Pt/C.

93. One or more ketones, alcohols, or branched alcohols produced according to any one of items 1 to 32, 39 to 40, or 46.

94. One or more alkanes, cyclic alkanes, or cyclic alcohols produced according to any one of items 33 to 38, 41 to 45, or 47 to 92.

95. A composition comprising:

a diesel fuel, a gasoline additive, or a lubricant, or any mixtures thereof; and one or more alkanes, cyclic alkanes, or cyclic alcohols produced according to any one of items 33 to 38, 41 to 45, or 47 to 92.

96. A method of producing one or more compounds of formula (IX), by contacting a ketone of formula (VII) with a diol of formula (VIII) to produce the one or more compounds of formula (IX), wherein:

the ketone of formula (VII) has the following structure:

(VII)

O $R_{14}$ $R_{15}$, wherein:

$R_{14}$ is H or alkyl; and $R_{15}$ is methyl;

the diol of formula (VIII) has the following structure:

(VIII)

HO $(\ )_t$ OH, wherein t is an integer greater than or equal to 4; and the one or more compounds of formula (IX) have the following structure:

(IX)

O $R_{14}$ $R_{16}$ $(\ )_t$ OH, wherein:

$R_{14}$ is as described above for formula (VII)

$R_{16}$ is —$CH_2$—; and t is as described above for formula (VIII).

97. The method of item 96, wherein t is an integer between 4 and 20.

98. The method of item 96 or 97, wherein:

the compound of formula (VII) is

O ;

the compound of formula (VIII) is

HO OH;

and the compound of formula (IX) is

O OH.

99. The method of any one of items 96 to 98, wherein the ketone of formula (VII) and the diol of formula (VIII) are further contacted with metal catalyst and optionally a base to produce the one or more compounds of formula (IX).

100. The method of item 99, wherein the metal catalyst comprises palladium.

101. The method of item 99, wherein the metal catalyst is Pd/C.

102. The method of any one of items 99 to 101, wherein the base is $K_3PO_4$.

103. The method of any one of items 96 to 102, further comprising hydrogenating one or more compounds of formula (IX) to one or more alcohols.

104. The method of item 103, further comprising converting the one or more alcohols to one or more alkenes or alkanes.

105. One or more alkene or alkanes produced according to the method of item 104.

The invention claimed is:

1. A method of producing one or more ketones by contacting a compound of formula (I) with a basic catalyst and one or more alcohols or aldehydes of formula (II) to produce the one or more ketones, wherein the compound of formula (I) and the compound of formula (II) have the following structures:

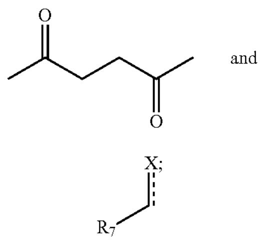

wherein:

$R_7$ is selected from the group consisting of alkyl, aryl, alkenyl, alkynyl, and heteroaryl;

X is OH or O; and the dashed line represents an optional double bond that is present when X is O; and wherein the basic catalyst:

(i) comprises an alkali metal hydroxide, an alkaline earth metal hydroxide, a mixed metal oxide, or $K_3PO_4$; or (ii) is a heterogeneous catalyst comprising Mg, Al, Zr, Ti, Ce, B, or Y, or any mixtures thereof.

2. The method of claim 1, wherein the compound of formula (II) is:

(II)

O, wherein $R_7$ is $C_1$-$C_{10}$ alkyl or $C_4$-$C_{21}$ heteroaryl.

3. The method of claim 1, wherein the compound of formula (II) is selected from the group consisting of furfural, 5-methylfurfural, and 5-hydroxymethylfurfural.

4. The method of claim 1, wherein the compound of formula (II) is:

(II)

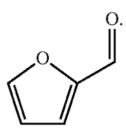

5. The method of claim 1, wherein the one or more ketones are selected from the group consisting of:

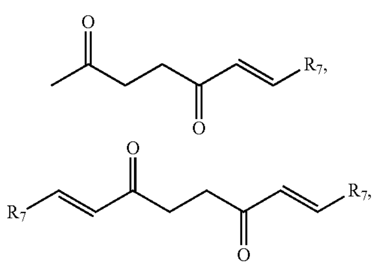

-continued

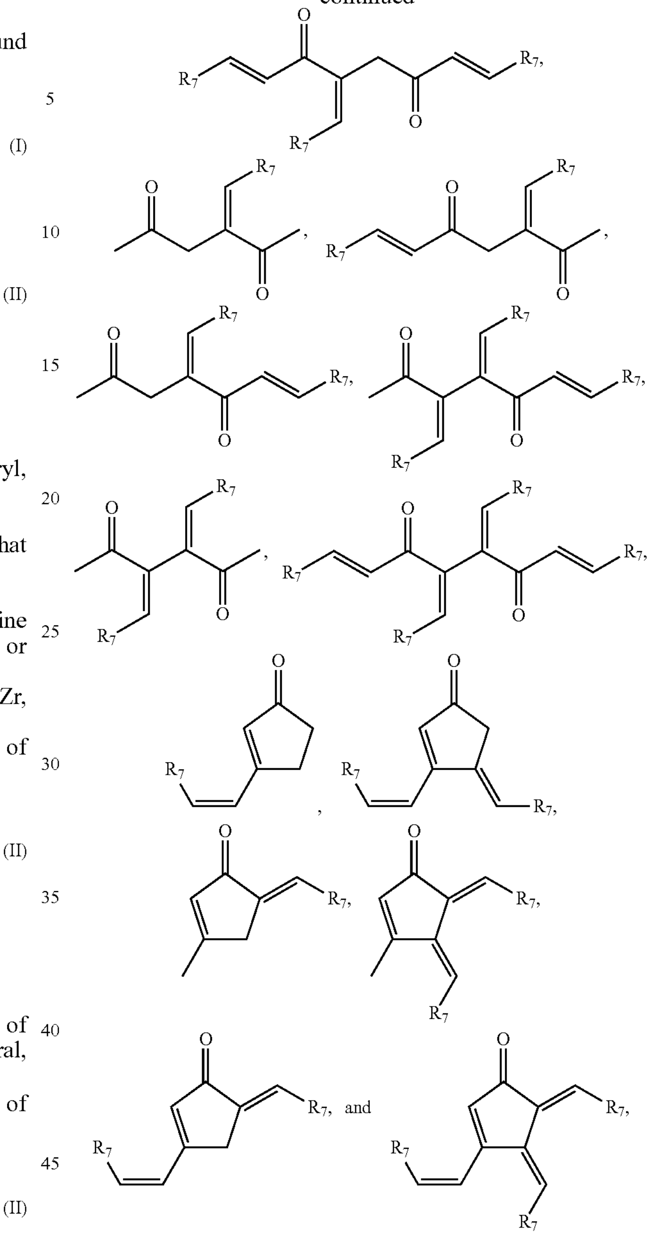

or any mixtures thereof.

6. The method of claim 1, wherein the basic catalyst comprises an alkali metal hydroxide, an alkaline earth metal hydroxide, or a mixed metal oxide.

7. The method of claim 6, wherein the mixed metal oxide comprises MgZrO or MgAlO.

8. The method of claim 1, wherein the compound of formula (I) is contacted with the basic catalyst in aqueous solvent, organic solvent, or biphasic aqueous and organic solvent.

9. The method of claim 8, wherein the organic solvent comprises toluene, trimethylacetonitrile, dimethylformamide, propyl-acetate, dioxane, butanol, hexanol, or octanol, or any mixture thereof.

10. The method of claim 1, wherein at least 70% of the one or more ketones are branched ketones.

11. The method of claim 1, further comprising hydrogenating the one or more ketones to one or more alkanes.

12. The method of claim 11, wherein the one or more alkanes are selected from the group consisting of:

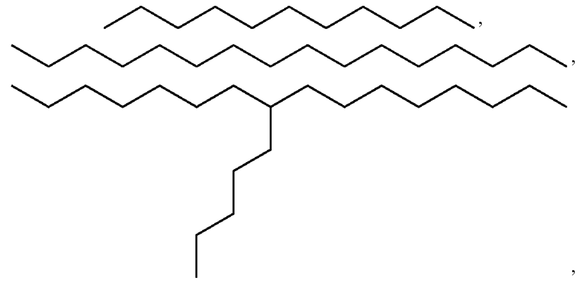

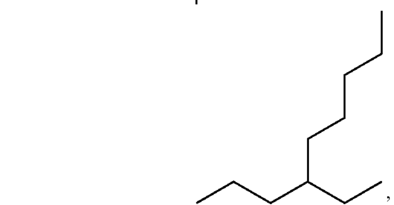

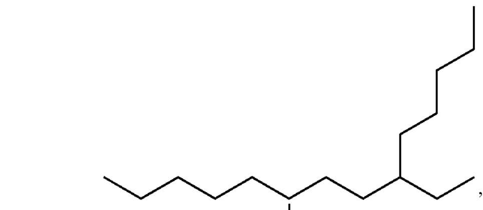

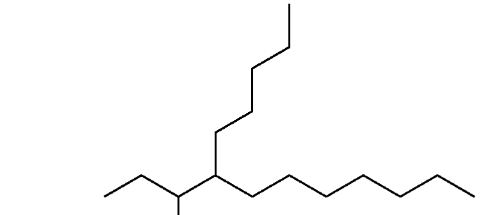

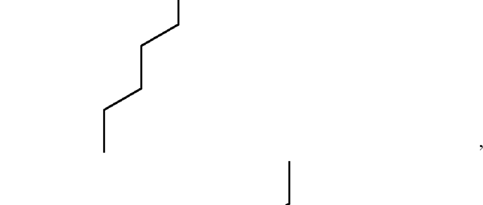

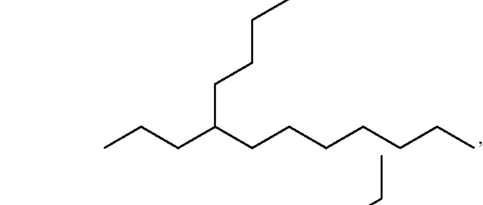

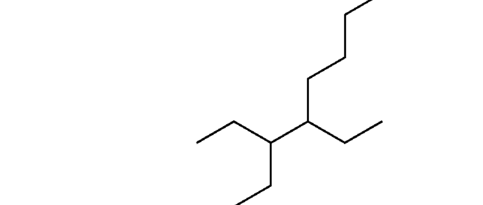

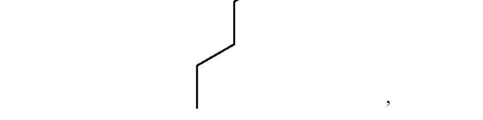

-continued

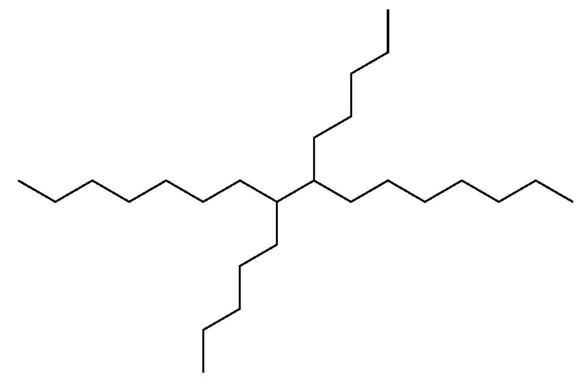

, and or any mixtures thereof.

13. The method of claim 1, wherein the basic catalyst comprises an alkali metal hydroxide, an alkaline earth metal hydroxide, a mixed metal oxide, or $K_3PO_4$.

14. The method of claim 1, wherein the basic catalyst is a heterogeneous catalyst comprising Mg, Al, Zr, Ti, Ce, B, or Y, or any mixtures thereof.

* * * * *